US008608758B2

(12) United States Patent
Singhatat et al.

(10) Patent No.: US 8,608,758 B2
(45) Date of Patent: Dec. 17, 2013

(54) THREADABLE KNOT SOFT TISSUE DEFECT REPAIR SYSTEM

(75) Inventors: Wamis Singhatat, West Chester, PA (US); Jamie Manos, West Chester, PA (US); Brian Rick Delamarter, Los Angeles, CA (US); Dominique Messerli, West Chester, PA (US); Brian Schmidt, West Chester, PA (US); William Miller, West Chester, PA (US); James Talbot, West Chester, PA (US); Garland Fussel, West Chester, PA (US); Nigel G. Smith, Norwich (GB)

(73) Assignee: DePuy Synthes Products, LLC, Raynham, MA (US)

( * ) Notice: Subject to any disclaimer, the term of this patent is extended or adjusted under 35 U.S.C. 154(b) by 594 days.

(21) Appl. No.: 12/722,134

(22) Filed: Mar. 11, 2010

(65) Prior Publication Data
US 2010/0249809 A1    Sep. 30, 2010

Related U.S. Application Data

(60) Provisional application No. 61/159,212, filed on Mar. 11, 2009.

(51) Int. Cl.
 *A61B 17/04* (2006.01)
 *A61B 17/10* (2006.01)
 *A61B 17/12* (2006.01)

(52) U.S. Cl.
 USPC ............................ 606/148; 606/139; 606/144

(58) Field of Classification Search
 USPC .................. 606/139, 144–148, 213
 See application file for complete search history.

(56) References Cited

U.S. PATENT DOCUMENTS

| 1,822,330 | A | * | 9/1931 | Ainslie ......................... 606/145 |
| 2,738,790 | A | * | 3/1956 | Todt, Sr. et al. ............... 606/145 |
| 5,059,201 | A | * | 10/1991 | Asnis ............................ 606/144 |
| 5,312,423 | A | * | 5/1994 | Rosenbluth et al. .......... 606/148 |
| 5,746,752 | A |  | 5/1998 | Burkhart |
| 5,792,151 | A | * | 8/1998 | Heck et al. .................... 606/144 |
| 5,816,258 | A |  | 10/1998 | Jervis |
| 5,868,762 | A |  | 2/1999 | Cragg et al. |
| 6,221,084 | B1 |  | 4/2001 | Fleenor |
| 6,245,079 | B1 | * | 6/2001 | Nobles et al. ................. 606/144 |
| 6,443,963 | B1 | * | 9/2002 | Baldwin et al. ............... 606/148 |

(Continued)

FOREIGN PATENT DOCUMENTS

| WO | WO 99/25254 | 5/1999 |
| WO | WO 02/22026 | 3/2002 |

OTHER PUBLICATIONS

U.S. Appl. No. 12/693,820, filed Jan. 26, 2010, Adams.

*Primary Examiner* — Dianne Dornbusch
(74) *Attorney, Agent, or Firm* — Woodcock Washburn LLP

(57) ABSTRACT

A soft tissue defect repair system for approximating defects, such as defects in the annulus fibrosus of an intervertebral disc, includes a cannulated rod through which is disposed a suture retrieval device. A strand of suture includes a locking or ratcheting knot pre-tied around the outside of the cannulated rod and a free end that is guided in and out of the soft tissue. A knot pusher fits around the cannulated rod, which is used to push the knot off of the cannulated rod after the stitching of the tissue is accomplished. The defect is approximated by tensioning the free end. Various suturing methods or patterns are disclosed for defect approximation.

19 Claims, 41 Drawing Sheets

(56) References Cited

U.S. PATENT DOCUMENTS

| | | | |
|---|---|---|---|
| 6,551,330 B1 * | 4/2003 | Bain et al. | 606/144 |
| 6,562,052 B2 * | 5/2003 | Nobles et al. | 606/144 |
| 6,770,084 B1 * | 8/2004 | Bain et al. | 606/144 |
| 6,893,448 B2 * | 5/2005 | O'Quinn et al. | 606/139 |
| 6,936,054 B2 * | 8/2005 | Chu | 606/145 |
| 7,118,583 B2 * | 10/2006 | O'Quinn et al. | 606/139 |
| 7,815,654 B2 * | 10/2010 | Chu | 606/144 |
| 2002/0045908 A1 | 4/2002 | Nobles et al. | |
| 2002/0156344 A1 | 10/2002 | Pasricha et al. | |
| 2005/0154402 A1 | 7/2005 | Sauer et al. | |
| 2008/0065156 A1 | 3/2008 | Hauser et al. | |

\* cited by examiner

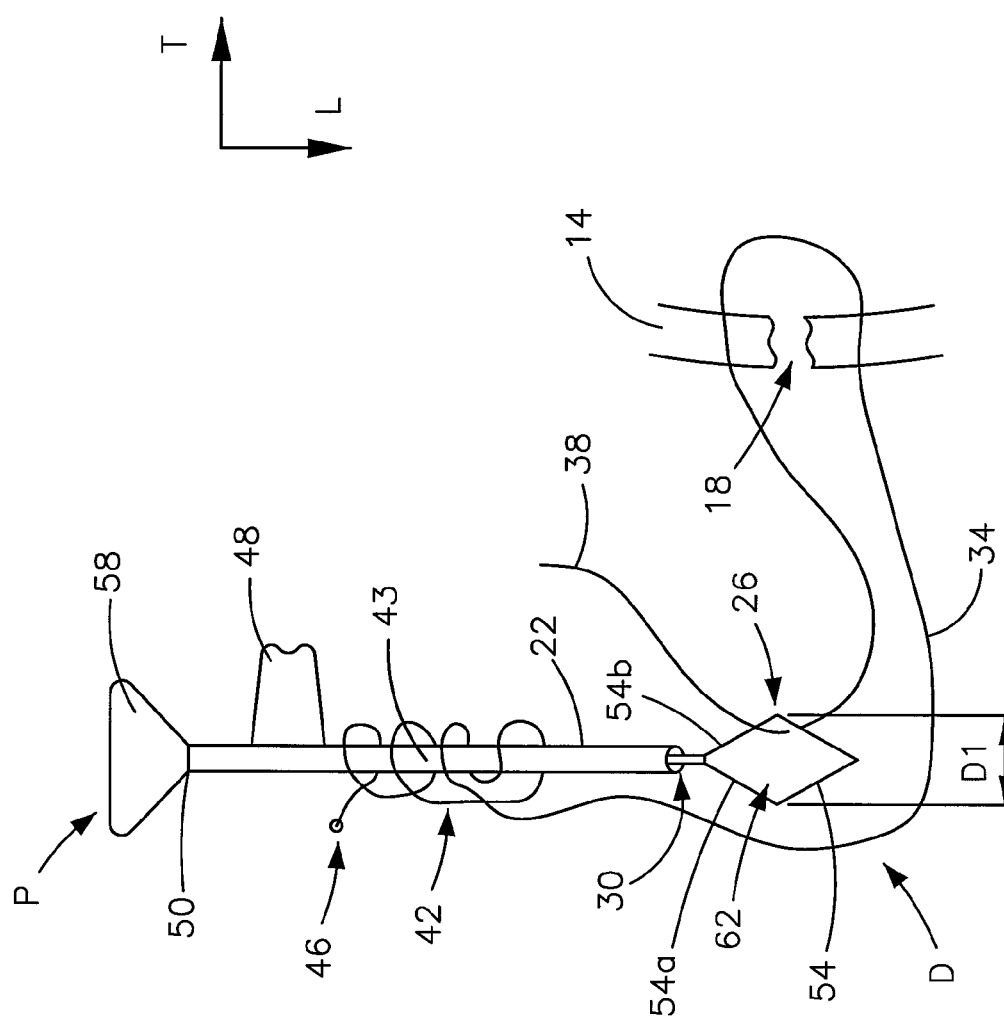

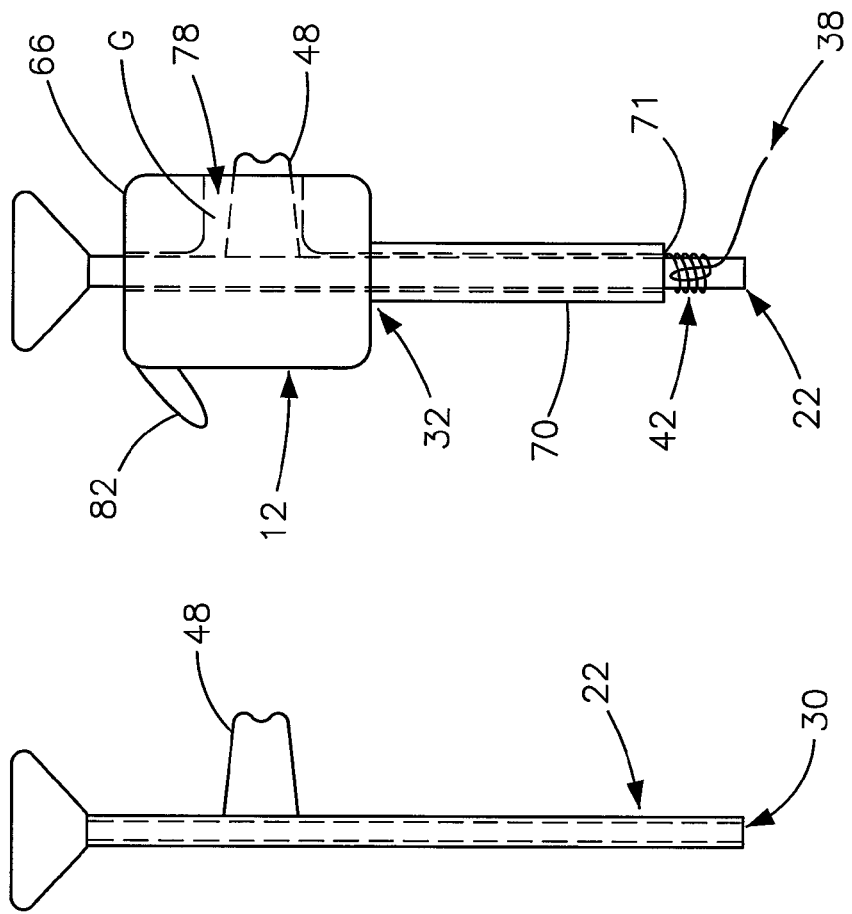
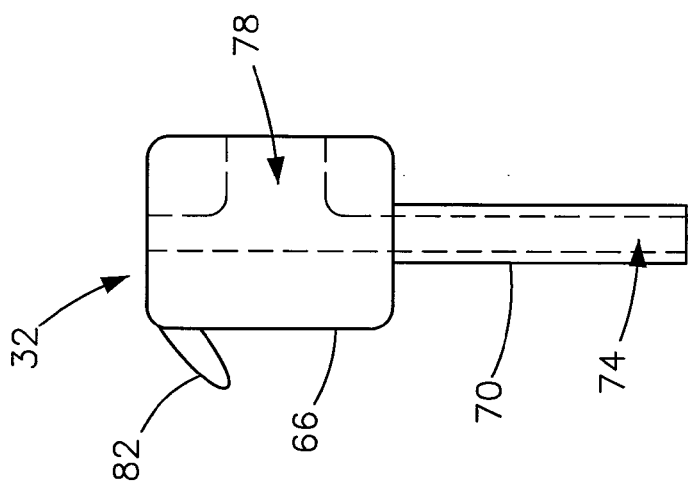
Fig. 3C
Fig. 3B
Fig. 3A

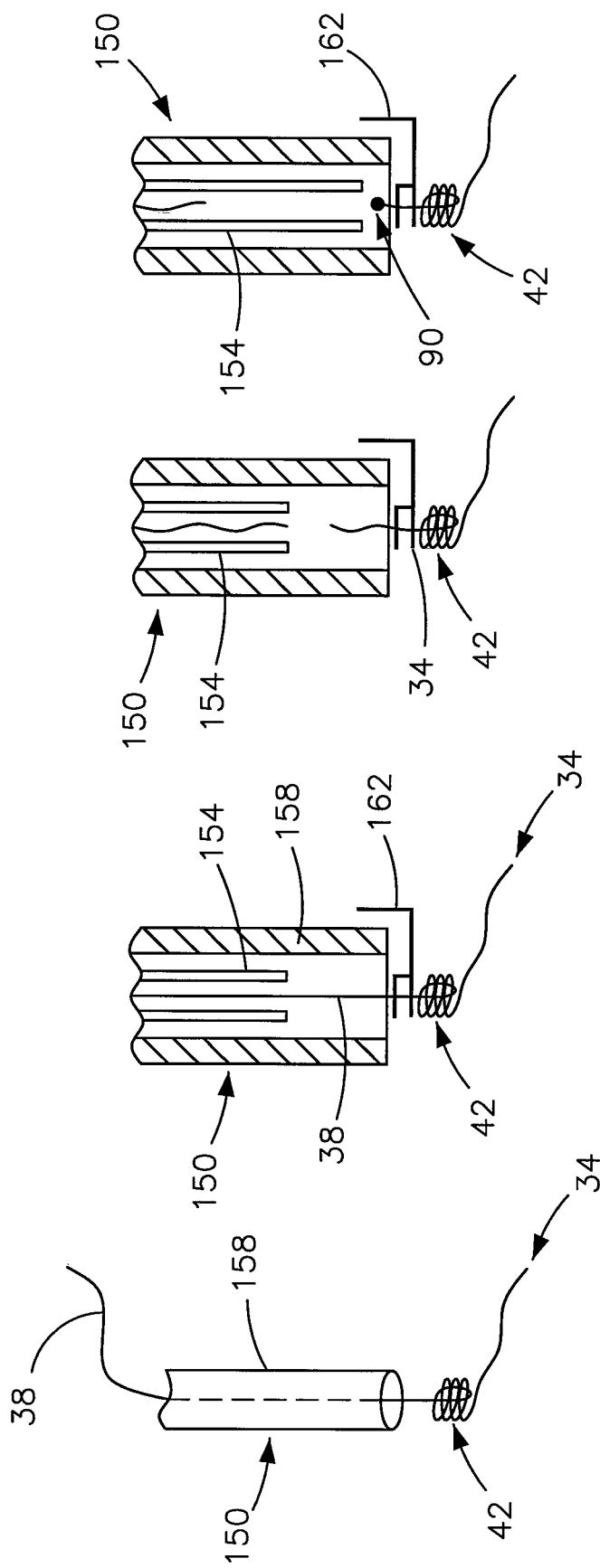

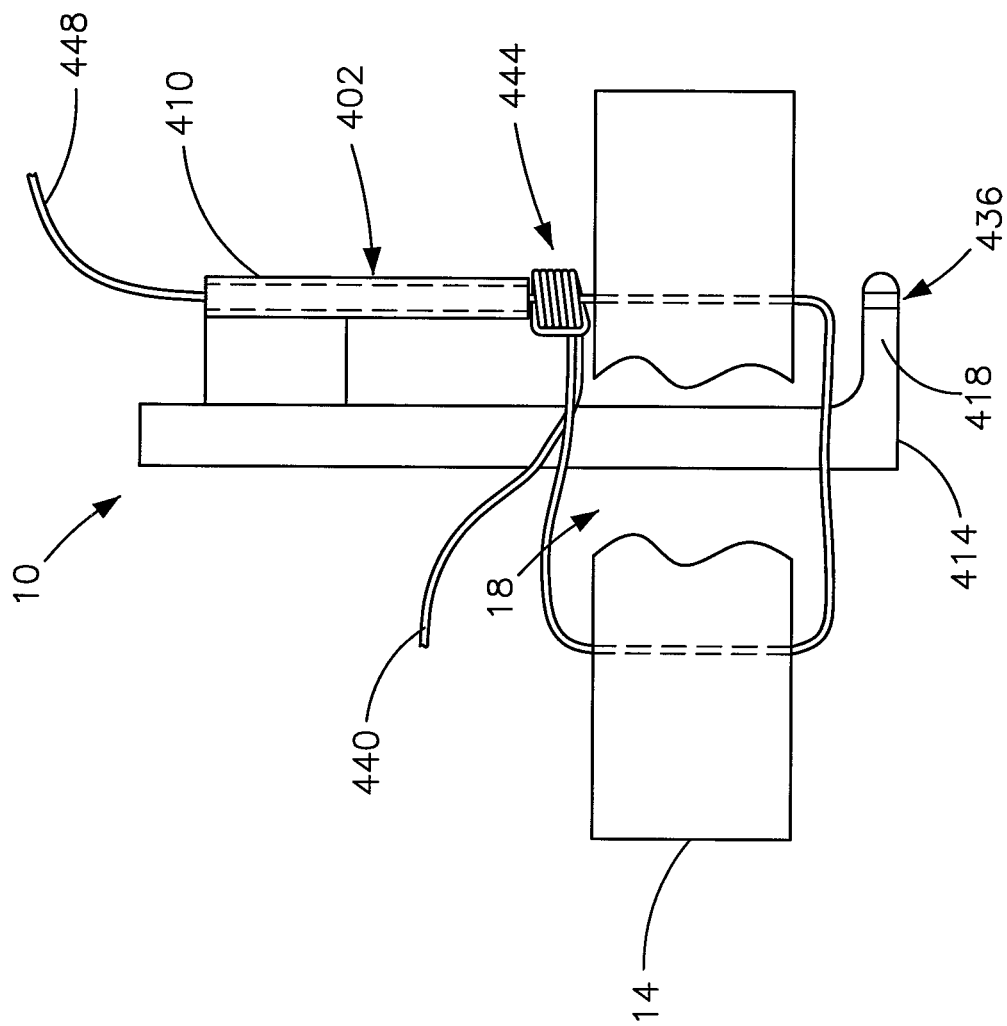

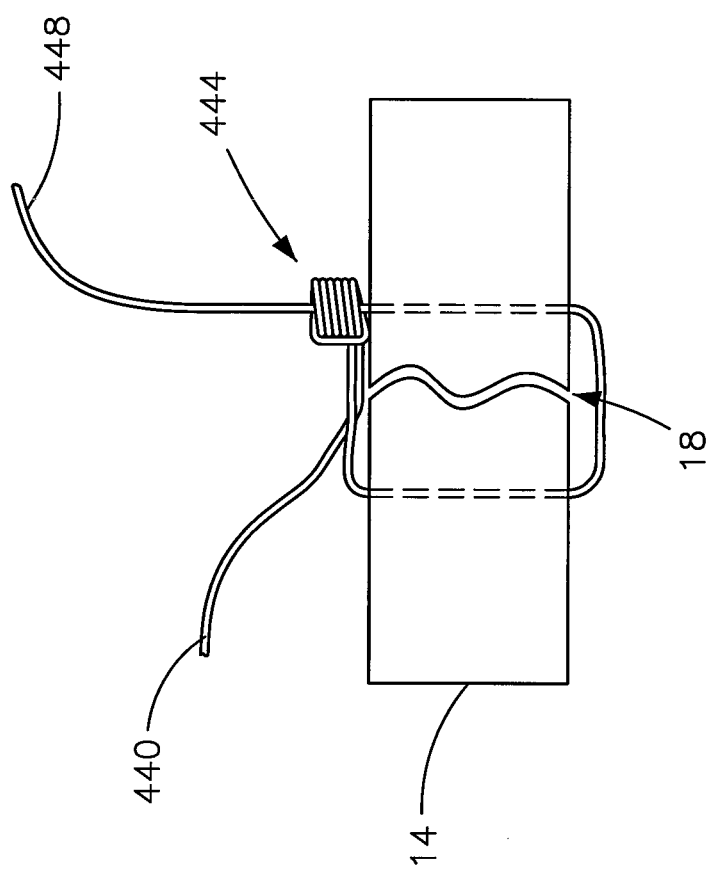

THREADABLE KNOT SOFT TISSUE DEFECT REPAIR SYSTEM

CROSS REFERENCE TO RELATED APPLICATIONS

This application claims priority to U.S. Provisional Application No. 61/159,212 filed Mar. 11, 2009, the contents of which are incorporated by reference in their entirety.

BACKGROUND OF THE INVENTION

A discectomy is a procedure that treats back pain, radiculopathy and/or myelopathy by surgically removing herniated nucleus pulposus to achieve neural decompression. Discectomy techniques involve removing intervertebral disc material through a hole in an annulus fibrosis of the disc, however such techniques typically do not repair the annular defect that is formed during the discectomy procedure. During the procedure, the surgeon may elect to remove only a herniated portion of nucleus impinging on the nerves, which treats the radiculopathy, but may increase the risk of post-operative reherniation of the remaining nucleus within the disc. Alternately, the surgeon may elect to perform extensive debulking, in which most of the remaining nucleus material is removed in addition to the herniated portion to minimize the risk of post-operative reherniation; however, the risk of post-operative disc height collapse and subsequent lower back pain may increase. Clinically patients tend to return to normal daily activities more quickly and suffer lessened disc degeneration when a limited discectomy is performed versus an extensive debulking of the disc. With current standard surgical practices, a hole or breach in an annulus is created, either pathologically due to a disc herniation, or by the surgeon during a nucleotomy or partial discectomy, and remains at the end of the procedure, leaving a pathway for future herniations.

BRIEF SUMMARY OF THE INVENTION

Various embodiments of a soft tissue repair system configured to repair soft tissue defects are disclosed. In one embodiment a soft tissue defect repair system includes a strand of surgical suture having a free end and a pre-tied knot, a rod about which the knot is tied, a suture retrieving device, and a knot pusher. The rod may include a channel and may extend along a longitudinal axis between a proximal end and a distal end. The suture retrieving device may be housed interior to and displaceable within the channel of the rod. The suture retrieving device may be retractably displaceable with respect to the proximal and distal ends of the rod and may be configured to capture the free end of the suture. When the free end of the suture strand is captured by the suture retrieving device, the suture retrieving device may pass the free end through the channel of the rod from the distal end, and out through the proximal end subsequent to the free end being passed through soft tissue adjacent the defect. The knot pusher may be coupled to the exterior of the rod, and may be configured to slide the knot distally off of the rod toward the defect.

In another embodiment the soft tissue repair system may include a longitudinally extending guide tube having a channel therethrough, and a boom arm extending from the guide tube. The boom arm may include a boom arm housing that is spaced from the guide tube, wherein a tissue-receiving gap is disposed between the boom arm housing and the guide tube. A needle may be reciprocally translatable within the channel of the guide tube between an advanced position in which a distal end of the needle extends into the boom arm housing, and a retracted position in which the distal end of the needle is retracted from the boom arm housing. The system may also include a shuttling element configured to detachably couple to the needle, and to the boom arm housing, and a strand of suture having a free end and a pre-tied knot, wherein the pre-tied knot is tied about the guide tube, and the free end is attached to the shuttling element.

Use of the disclosed systems will gain the post-operative benefits afforded by a limited discectomy technique while providing a barrier against reherniation. Simplicity of the systems is key, as standard discectomy procedures typically last less than 40 minutes, and it is undesirable to keep a patient under general anesthesia longer than necessary. Therefore, the disclosed invention and its embodiments allow for a simple annulus closure solution.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the soft tissue defect repair systems of the present application, there is shown in the drawings preferred embodiments. It should be understood, however, that the application is not limited to the precise arrangements and instrumentalities shown. In the drawings:

FIG. 2A is a front elevation view of the cannulated rod and the suture retrieval device of FIG. 1 prior to translating the suture retrieval device through the cannulated rod, the knot pusher is removed for clarity;

FIG. 3A is an enlarged front elevation view of the knot pusher of the soft tissue defect repair system illustrated in FIG. 1;

FIG. 3B is an enlarged front elevation view of the cannulated rod illustrated in FIG. 1;

FIG. 3C is an enlarged front elevation view of the knot pusher illustrated in FIG. 3A installed onto the cannulated rod illustrated in FIG. 3B;

FIG. 5A is a front elevation view of a heat cutting instrument in accordance with an embodiment of the present invention;

FIG. 5B is a cross-sectional view of the heat cutting instrument shown in FIG. 5A;

FIG. 5C is a cross-sectional view of the heat cutting instrument shown in FIG. 5B with the suture strand severed;

FIG. 5D is a cross-sectional view of the heat cutting instrument shown in FIG. 5C with the suture strand heated to form a ball;

FIG. 13F is a cross-sectional view of the soft tissue defect repair system of FIG. 13E, showing a sixth step of using the soft tissue defect repair system;

FIG. 13G is a cross-sectional view of the soft tissue defect repair system of FIG. 13F, showing a seventh step of using the soft tissue defect repair system;

DETAILED DESCRIPTION OF THE INVENTION

Figure 1:
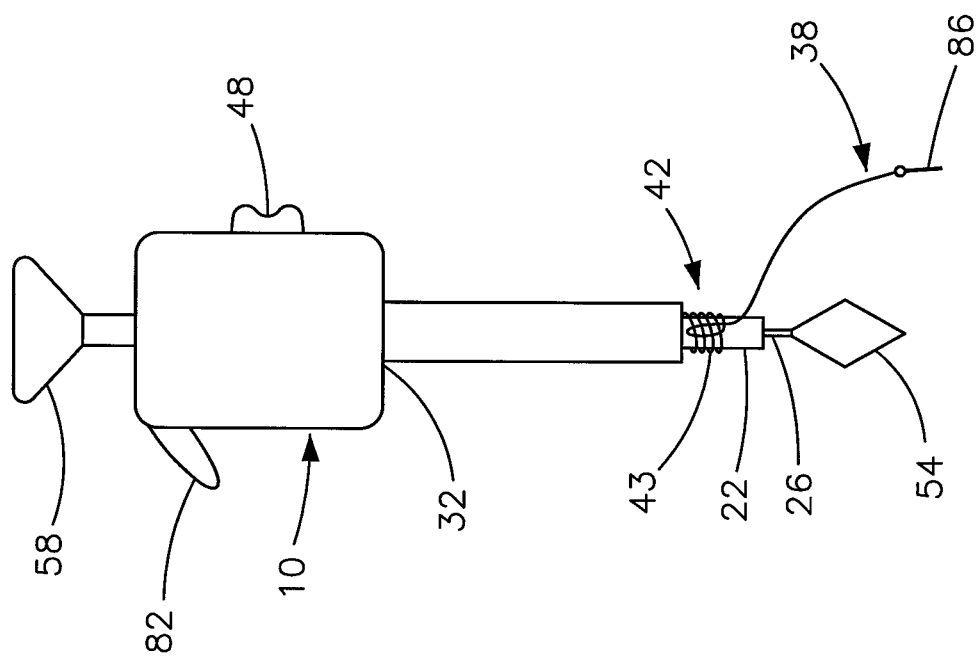
FIG. 1 is a front elevation view of an embodiment of an assembled soft tissue defect repair system including a cannulated rod, a suture retrieval device, and a knot pusher.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the preferred soft tissue defect repair systems and related parts thereof. The words, "anterior", "posterior", "superior," "inferior", "medial", "lateral" and related words and/or phrases designate preferred positions and orientations in the human body to which reference is made and are not meant to be limiting. The terminology includes the above-listed words, derivatives thereof and words of similar import.

In reference to FIGS. 1-3C, a soft tissue defect repair system 10 constructed in accordance with one embodiment is configured to help repair a soft tissue 14, such as the annulus fibrosis of an intervertebral disc, having a defect 18, such as a fissure. The soft tissue defect repair system 10 may include a suture finishing device 12 that is elongate in a longitudinal direction L, and includes a proximal end P and an opposing distal end D. As shown, the suture finishing device 12 includes a cannulated rod 22 that is elongate in the longitudinal direction L, a suture retrieval device 26 translatable along the direction L within a channel 30 of the cannulated rod 22, and a knot pusher 32 disposed about the cannulated rod 22. The suture finishing device 12 can also include a strand of surgical suture 34 having a first free end 38, a knot 42, and a second free end which may be configured to truncate in a suture ball 46. The knot 42 is a pre-tied threadable knot that is tied about a target knot location 43 of the cannulated rod 22, which is disposed between the proximal end and the distal end of the cannulated rod 22. Use of a pre-tied threadable knot in combination with a number of suture passing techniques and stitch configurations may allow for the placement of a full thickness stitch that is secured to the tissue with a "zero" profile on the outer annulus wall and may drastically reduce surgical time over manual knot tying. Knot 42 may be created using any method known, including the methods disclosed for preparing knot 534 of FIGS. 14B and 14C. In accordance with one embodiment, the knot location 43 can be at or proximate to the distal end of the cannulated rod 22. Otherwise stated, the knot 42 can be tied about the distal end of the cannulated rod 22 prior to or during the surgical procedure. In this regard, it should be appreciated that the soft tissue defect repair system 10 can also be provided without the strand of surgical suture 34, which can be added to the soft tissue defect repair system 10 by the surgeon prior to or during the surgical procedure. The soft tissue defect repair system 10 can thus be provided as a disposable or a reusable system.

The knot 42 can assume the form of a sliding knot, a ratcheting knot, or other various types of locking knots known in the field of surgery. In a preferred embodiment, the knot 42 is a ratcheting or locking knot configured to prevent postoperative loosening of the repaired construct. As shown in FIG. 2A, the knot 42 has a free proximal end, which can be provided as a suture ball 46, such as bulk of melted or singed suture material having a diameter greater than that of the suture strand 34 of the knot 42. The suture ball 46 can be provided by cutting the suture strand 34 and applying heat as described in detail below with reference to FIGS. 5A-5D. The suture ball 46 can serve to prevent the knot 42 from unraveling. Alternatively, the suture strand 34 may have an uncut second free end instead of a second free end formed into a suture ball 46, as shown in reference to knot 534 of FIG. 14B.

As shown in FIGS. 2A-2D, the cannulated rod 22 is preferably a hollow tube, and the channel 30 extends along the direction L entirely therethrough. The suture retrieval device 26 extends through the channel 30, and the knot 42 is disposed about an exterior surface of the cannulated rod 22 proximate to a distal end of the rod 22. The cannulated rod 22 may also include a knob 48 extending transversely from a proximal end of the rod 22. The cannulated rod 22 preferably serves as a temporary "post strand" that allows the first free end 38 of the suture strand 34 to be passed through the soft tissue 14 on either side of the defect 18.

Figure 2D:
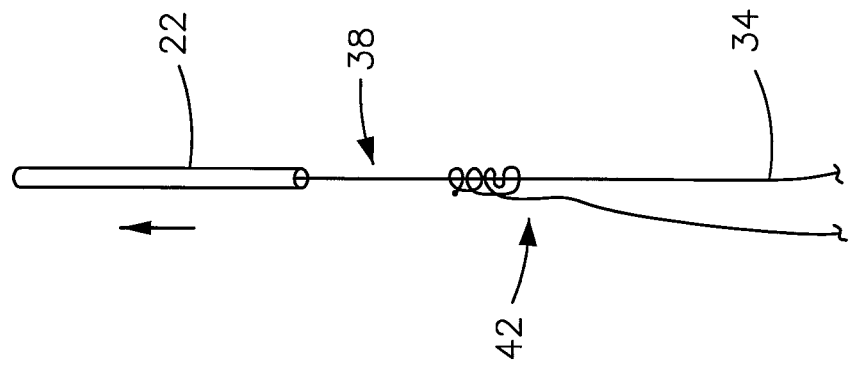
FIG. 2D is a perspective view of a portion of the soft tissue defect repair system illustrated in FIG. 2A, showing the threadable knot pushed off of the cannulated rod.
Figure 2C:
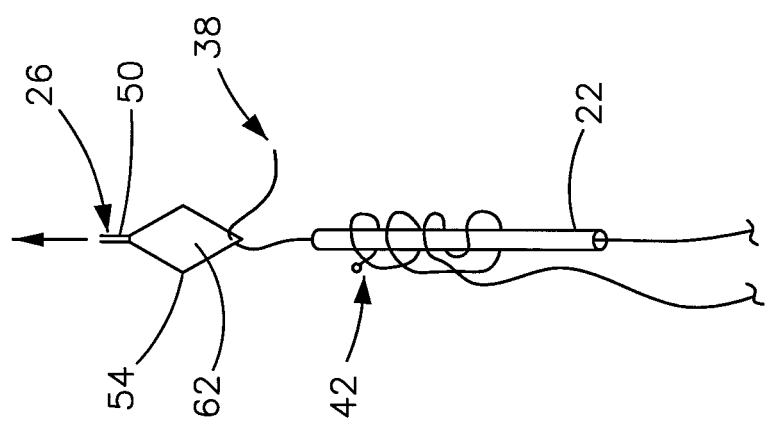
FIG. 2C is a front elevation view of the soft tissue defect repair system illustrated in FIG. 2A, showing the suture retrieval device after translation through the cannulated rod.
Figure 2B:
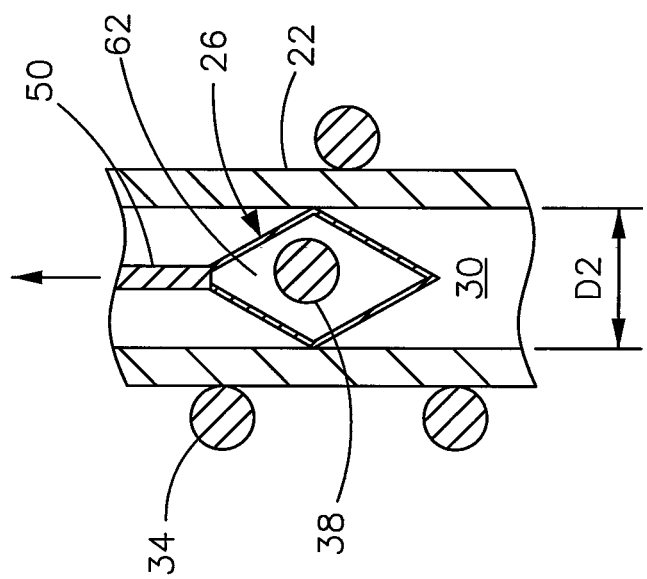
FIG. 2B is an enlarged sectional front elevation view of the soft tissue defect repair system illustrated in FIG. 2A, showing the suture retrieval device being translated through the cannulated rod in a compressed configuration.

The suture retrieval device 26 includes a shaft 50, a flexible knot threader 54 extending from the distal end of the shaft 50, and a handle 58 extending from the proximal end of the shaft 50. The flexible knot threader 54 defines an opening 62 that receives and captures the first free end 38 of the suture strand 34. The knot threader 54 can be diamond shaped or alternatively shaped as desired, and is made of a compressible wire-like material. As shown in FIG. 2A, the shaft 50 extends through channel 30 of the cannulated rod 22 with the threader 54 extending out from a distal end of the rod 22, and the handle extending out from a proximal end of the rod 22. As shown in FIG. 2B, when handle 58 is pulled, the shaft 50 is translated proximally with respect to the cannulated rod 22, thereby pulling threader 54 against a distal end of rod 22 and causing it to collapse on itself or compress so that it may be pulled through the channel 30 of the rod 22.

For instance, as illustrated in FIG. 2A, the threader 54 defines a pair of outer surfaces 54a and 54b that are opposed along a direction T transverse to the longitudinal direction L. The outer surfaces 54a and 54b define an initial outer transverse dimension $D_1$ when the threader 54 is not disposed in the channel 30, and thus is in a relaxed or neutral configuration. As shown, $D_1$ is large enough to provide easy access for a user to thread the first free end 38 of the suture strand 34 therethrough. That is, D1 is large enough, such that opening 62 provides a window for an individual to easily pass the first free end 38 of the suture strand 34 therethrough. Referring to FIG. 2B, as the threader is drawn into the channel 30, the outer surfaces 54a and 54b compress inward toward each other, thereby defining a compressed outermost transverse dimension $D_2$ that is less than the initial outer transverse dimension $D_1$. In accordance with the illustrated embodiment, the initial transverse dimension $D_1$ is greater than the inner diameter of the channel 30, and the compressed transverse dimension $D_2$ is substantially equal to the inner diameter of the channel 30, so that the threader can be drawn through the channel 30 during use. When compressed, threader 54 may pinch the first free end 38 of the suture strand 34 so that the first free end 38 does not unintentionally fall from the suture retrieval device 26. While threader 54 is described as being flexible, it should be understood that the threader 54 may also be a rigid hook.

Referring now to FIGS. 3A-3C, the suture finishing device 12 also includes a knot pusher 32, having a proximally disposed handle portion 66, and a shaft portion 70 extending distally from the handle portion 66. The shaft portion 70 terminates at a distal pusher surface 71 that is disposed proximally with respect to the knot 42, and aligned with the knot 42. Thus, movement of the shaft portion 70 distally with respect to the rod 22 (or movement of the rod 22 proximally with respect to the pusher 32) causes the pusher surface 71 to push the knot 42 distally off of the cannulated rod 22. A channel 74 extends longitudinally through both the handle portion 66 and the shaft portion 70. The knot pusher 32 also includes a transverse recess 78 disposed interior to the handle portion 66 that connects the longitudinal channel 74 to the exterior of the handle portion 66. The longitudinal channel 74 and the transverse recess 78 are preferably configured to house the cannulated rod 22 and the knob 48, respectively. The recess 78 extends longitudinally a distance greater than the knob 48, such that a longitudinal gap G allows the pusher 32 to translate distally along the rod 22. Once the pusher surface 71 has pushed the knot 42 off the rod 22, the knob 48 abuts the handle 66 at the proximal end of the recess 78 to prevent the knot pusher 32 from sliding off the rod 22. The knot pusher 32 may also include a suture cleat 82, which can extend out from the handle portion 66, for instance at the proximal end of the handle portion 66.

In operation, and referring now to FIGS. 1-3C, the soft tissue defect repair system 10 is utilized to help repair a soft tissue defect 18 of soft tissue 14 such as a fissure of an annulus fibrosis of the intervertebral disc. The suture retrieval device 26 is inserted through the cannulated rod 22 such that the flexible knot threader 54 protrudes from the distal end of the cannulated rod 22 and the handle portion 58 protrudes from the proximal end of the cannulated rod 22. The knot 42 and ball 46 (or second free end) of the suture strand 34 are disposed around the cannulated rod 22, and the cannulated rod 22 is inserted into the longitudinal channel 74 of the knot pusher 32 such that the knob 48 of the cannulated rod 22 is housed interior to the transverse recess 78 of the knot pusher 32. The first free end 38 of the suture strand 34 is connected to a needle 86, and is passed from the exterior through the entire thickness of the soft tissue 14 on a first side of the defect 18, passed under and to an opposite side of the defect 18, and passed to the exterior on the second, opposite side of the defect 18 using, for example, a curved or straight needle having an eyelet. The needle 86 does not have to have an eyelet, and thus the suture strand 34 may be coupled directly to the needle 86. This step may be repeated several times if desired, depending on the size of the defect 18. This step may also be reversed so that the suture is passed first from an interior surface to an exterior surface of the tissue 14, passed over the exterior of the tissue, then passed from the exterior to the interior of the tissue 14. This ordering of steps will result in the knot 42 residing on the interior surface of the tissue 14.

The knot threader 54 of the suture retrieval device 26 is then implemented to capture the first free end 38 after the needle 86 is removed. For instance, the first free end 38 is inserted through the opening 62 of the retrieval device 26 as illustrated in FIG. 2A. As the handle 58 of the suture retrieval device 26 is pulled proximally, the knot threader 54 is drawn proximally through the cannulated rod 22 as shown in FIG. 2B, causing the first free end 38 to also travel proximally through the cannulated rod 22 along with the knot threader 54. The compression of the knot threader further assists in retaining the first free end 38 through the opening 62. The handle 58 is further pulled proximally until the knot threader 54 is pulled proximally out of the cannulated rod 22 as shown in FIG. 2C, thereby threading the first free end 38 through the knot 42 which is disposed about the cannulated rod 22. Hence, the knot 42 can be referred to as a threadable knot. The defect 18 is approximated by pulling the first free end 38 in tension, thereby drawing the cannulated rod 22 and knot 42 to the defect 18. The knot pusher 32 is then translated distally until the distal pusher surface 71 pushes the knot 42 distally off of the cannulated rod 22 to the site of the defect 18. Alternatively, the rod 22 can be translated proximally until the distal pusher surface 71 of the knot pusher 32 pushes the knot 42 distally off of the cannulated rod 22 to the site of the defect 18.

The knot 42 then tightens around the first free end 38 by pulling on the first free end or free ends to "dress" the knot, and then by pulling on the first free end to slide the knot distally until the defect is re-approximated, allowing the loop of the suture strand 34 to remain secured in the approximated position. Once the knot 42 is fully tightened in its final placement, the first free end 38 or ends are cut using, for example, a suture blade or micro-scissors (not shown), thereby completing the repair of the defect 18 (for example as shown in FIG. 13G).

Figure 6B:
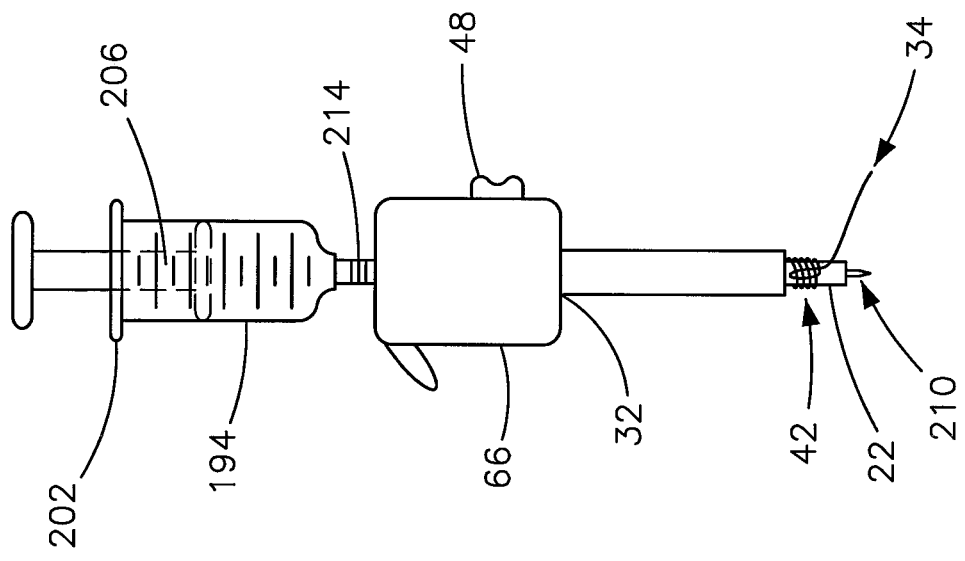
FIG. 6B is a front elevation view of the applicator instrument shown in FIG. 6A coupled to the soft tissue repair system shown in FIG. 3.
Figure 6A:
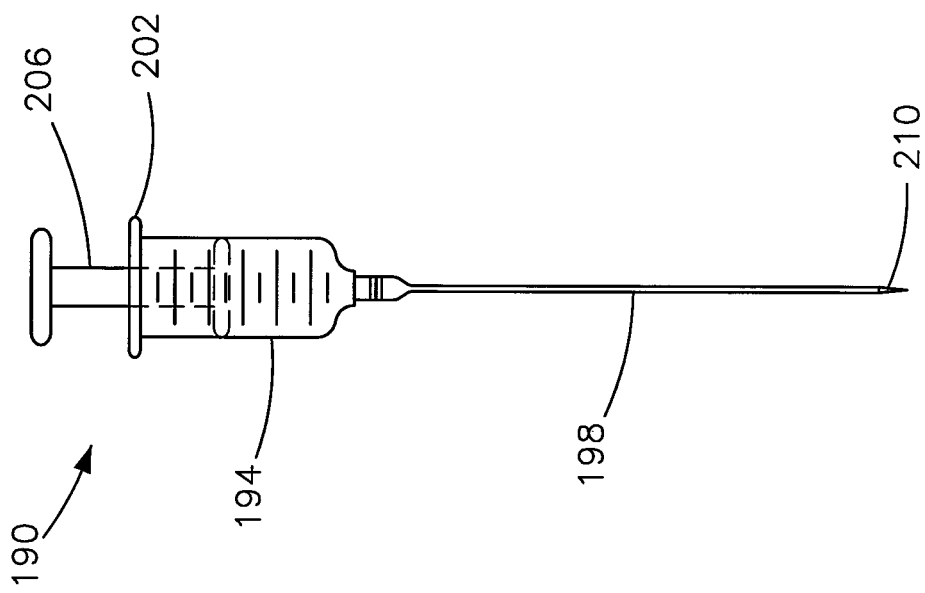
FIG. 6A is a front elevation view of an embodiment of an applicator instrument of the present invention.

A heat cutting device, as described below with reference to FIGS. 5A-5D, and/or an adhesive applicator, as described below with reference to FIGS. 6A-6B, may be implemented to secure the approximation. For example a heat cutting device, can be utilized to cut and/or melt the first free end 38, thereby forming a second suture ball 90, which serves to prevent the knot 42 from unraveling. A biocompatible adhesive, such as fibrin glue or biocompatible cyanoacrylate, can also be utilized to further secure the knot 42. The adhesive can be applied either immediately before or immediately after cutting the first free end 38. A suitable embodiment of an apparatus for applying the adhesive is illustrated in FIGS. 6A-6B. The inclusion of such an adhesive may additionally assist in maintaining the approximation of the soft tissue 14.

Figure 4C:
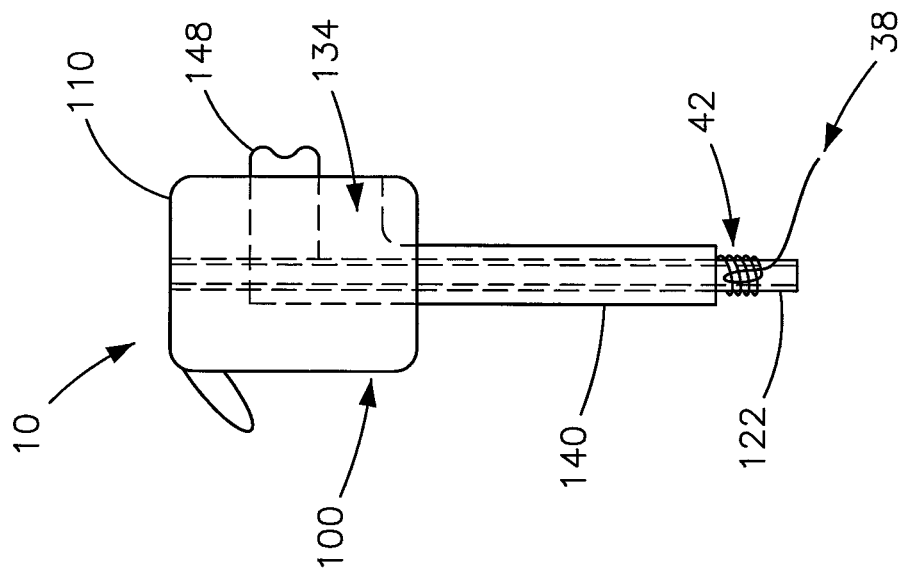
FIG. 4C is an assembled view of the knot pusher portion of FIG. 4B, and cannulated rod portion of FIG. 4A.
Figure 4B:
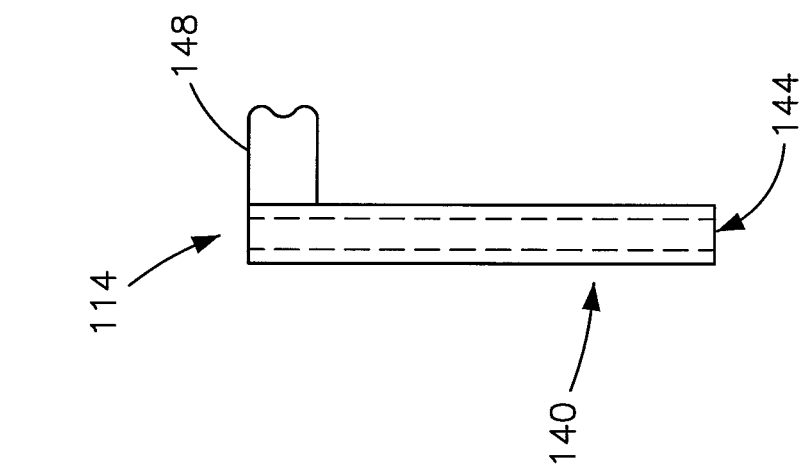
FIG. 4B is an enlarged front elevation view of a knot pusher according to another embodiment of the soft tissue defect repair system.
Figure 4A:
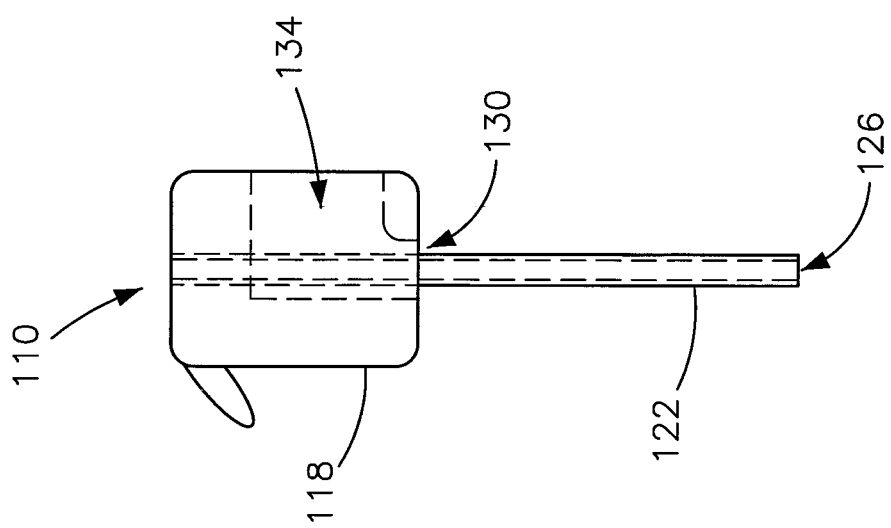
FIG. 4A is an enlarged front elevation view of a cannulated rod according to another embodiment of the soft tissue defect repair system.

In another embodiment, and in reference to FIGS. 4A and 4B, the cannulated rod and the knot pusher may be reversed. Instead of disposing the knob 48 near the proximal end of the cannulated rod 22 such that retracting the cannulated rod 22 proximally with respect to the knot pusher 32 pushes the knot 42 distally off of the cannulated rod 22, as is described in reference to FIGS. 1-3C, a similar knob can be disposed near the proximal end of the knot pusher, such that advancing the knot pusher distally with respect to a cannulated rod forces the knot distally off of the cannulated rod. For example, as shown in FIGS. 4A-4C, the soft tissue repair system 10 may include a suture finishing device 100. As shown, the suture finishing device 100 may include a cannulated rod 110 combined with a knot pusher 114. As shown, cannulated rod 110 includes a handle portion 118 and a shaft portion 122 extending through the handle portion 118 and distally from a bottom of the handle portion 118. As shown, a longitudinal channel 126 extends through the entire longitudinal length of the shaft portion 122, and is configured to house a suture retrieval device, such as suture retrieval device 26 shown in FIGS. 2A-2C. The handle portion 66 includes a longitudinal channel 130 and a transverse recess 134 disposed interior to the handle portion 118 that connects the longitudinal channel 130 to the exterior of the handle portion 118.

As shown in FIG. 4A, the knot pusher 114 includes a tube-like body 140 having a channel 144 extending the entire longitudinal length of the body 140. The knot pusher 114 also includes a knob 148 extending transversely from a proximal end of the body 140.

As shown in FIG. 4B, the knot pusher 114 may be housed within channel 130 and recess 134 of the cannulated rod 110 such that the knob 148 of the knot pusher 114 extends from the housing portion of the cannulated rod 110. When combined, the shaft portion 122 of the cannulated rod 110 extends through the channel 144 of the knot pusher 114 such that the knot pusher 114 may be translatable along the shaft portion 122. In operation, the knot pusher 114 may be advanced distally along the shaft portion 122 of the cannulated rod 110 to thereby push the pre-tied knot off of the distal end of the shaft portion 122.

In reference to FIGS. 5A-5D, a heat cutting instrument 150 may be utilized to cut and melt the first free end 38 of the suture strand 34 and thereby form the ball 90. The heat cutting instrument 150 includes a retractable heat cutter 154 surrounded by a shielding element 158 that is configured to protect surrounding tissue from being damaged or necrosing, and a distally disposed knot shield 162 configured to protect the knot 42 from being damaged by the heat cutter 154.

In operation, and in continuing reference to FIGS. 5A-5D, the heat cutting instrument 150 is placed over the suture strand 34 such that the heat cutter 154 is slightly spaced from the knot 42. Power is supplied to the heat cutting instrument 150, causing the heat cutter 154 to emanate heat sufficient to cause the suture strand 34 to melt and sever to form a cut end, as shown in FIG. 5C. The heat cutter 154 is then advanced distally with respect to the heat cutting instrument 150 and toward the knot 42, causing the cut end of the severed suture strand 34 to melt and shrivel into the ball 90, as shown in FIG. 5D. The heat cutter 154 advances and draws with it the forming ball 90 until the ball 90 is adjacent to the knot 42, while the shield 158 protects adjacent tissues and the knot shield 162 protects the knot 42 from the heat emitted by the heat cutter 154. The formed ball 90 assists in preventing the knot 42 from unraveling. The heat cutting instrument 150 may be utilized to form the knot 42 intra-operatively, pre-operatively, or during manufacturing and assembly of the soft tissue defect repair system 10.

In reference to FIGS. 6A and 6B, an adhesive applicator instrument 190 and a suitable coupling configuration 194 for coupling the adhesive applicator instrument 190 to the knot pusher 32 and cannulated rod 22 assembly is illustrated. The adhesive applicator instrument 190 assumes the form of a syringe injector that is configured for dispensing adhesive such as fibrin glue or biocompatible cyanoacrylate. The adhesive applicator instrument 190 includes a tubular casing 194 from which is distally appended a needle portion 198. A handle 202 is disposed at the proximal end of the tubular casing 194. A plunger 206 is reciprocally coupled to the interior of the tubular casing 194 to displace an amount of adhesive 210 housed interior to the tubular casing 194 through the adhesive applicator instrument 190 and out the distal end of the needle 198. Disposed near the distal end of the tubular casing 194 is a connector 214, such as a luer lock or a series of threading, configured to couple the adhesive applicator instrument 190 to the knot pusher 32 and cannulated rod 22 assembly.

In operation, the adhesive applicator instrument 190 can be utilized to apply a desired amount of biocompatible adhesive 210 to further secure the knot 42 near the defect 18. The adhesive applicator instrument 190 is inserted through the knot pusher 32 and cannulated rod 22 assembly and coupled thereto via the coupling 194, such as a luer lock, and a corresponding coupling mechanism (not shown) included at the proximal end of the handle portion 66. The plunger 206 is displaced toward the distal end to expel a desired amount of adhesive 210 either just prior to or subsequent to approximation of the defect 18. The adhesive applicator instrument 190 can be inserted through the knot pusher 32 and cannulated rod 22 assembly with or without the needle portion 198. The adhesive applicator instrument 190 can further be utilized separately from the knot pusher 32 and cannulated rod 22 assembly, and can be used in addition to or instead of the ball 90 formed by the heat cutting instrument 150.

Figure 7:
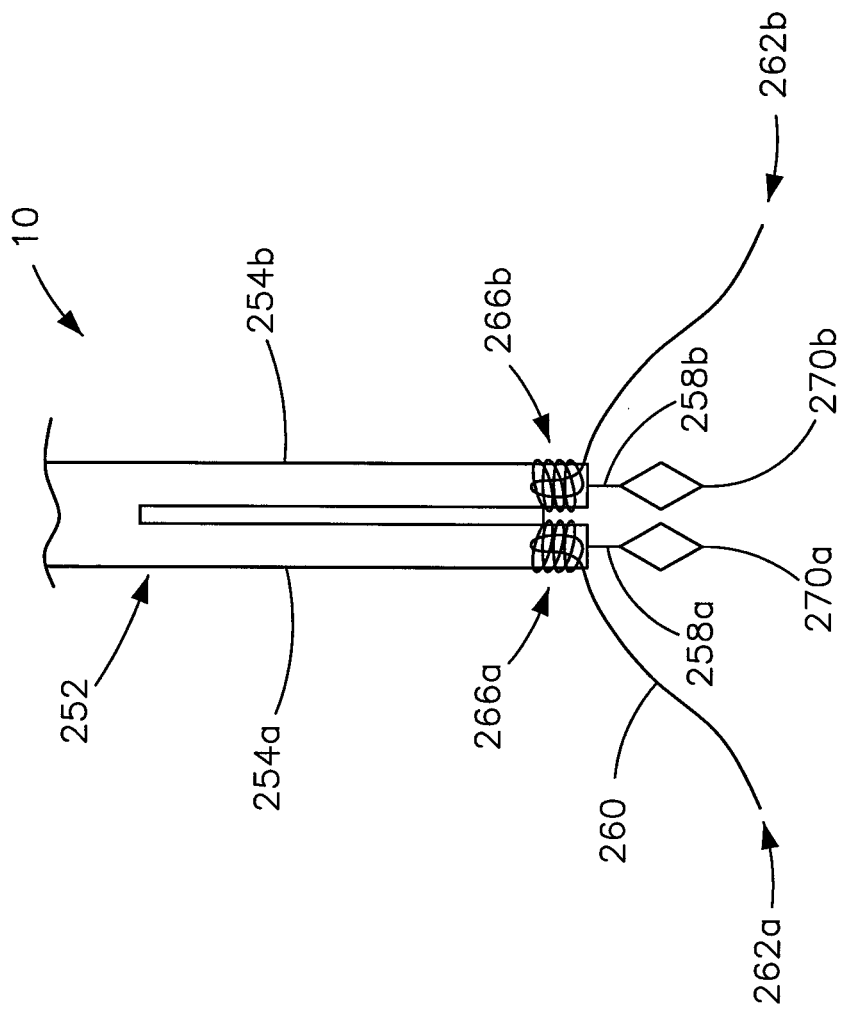
FIG. 7 is a front elevation view of a soft tissue defect repair system in accordance with another embodiment of the present invention.
Figure 8B:
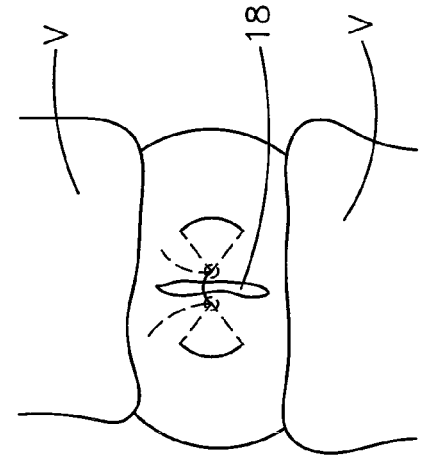
FIGS. 8A-8B are front elevation views of the system shown FIG. 7 repairing a soft tissue defect in accordance with an example method.
Figure 8D:
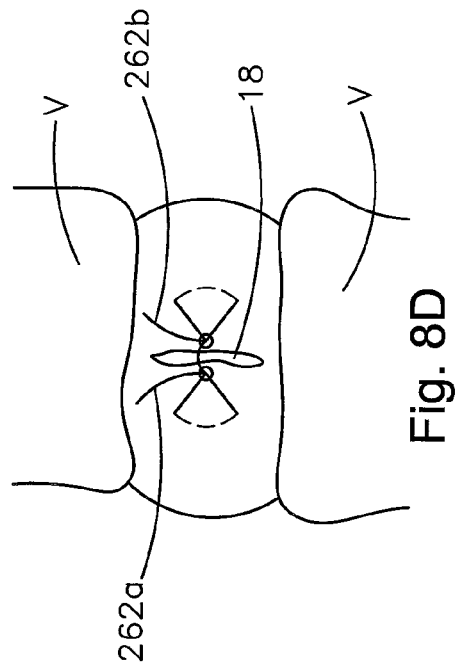
FIGS. 8C-8D are front elevation views of the system shown FIG. 7 repairing a soft tissue defect in accordance with another example method.
Figure 8A:
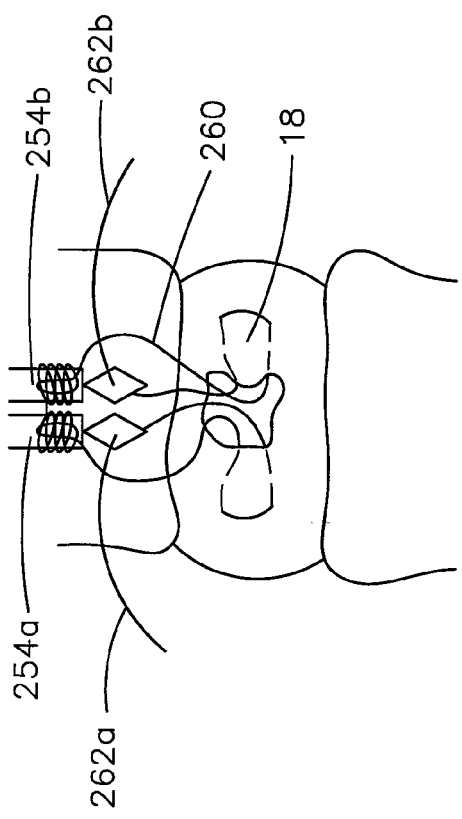
Figure 8C:
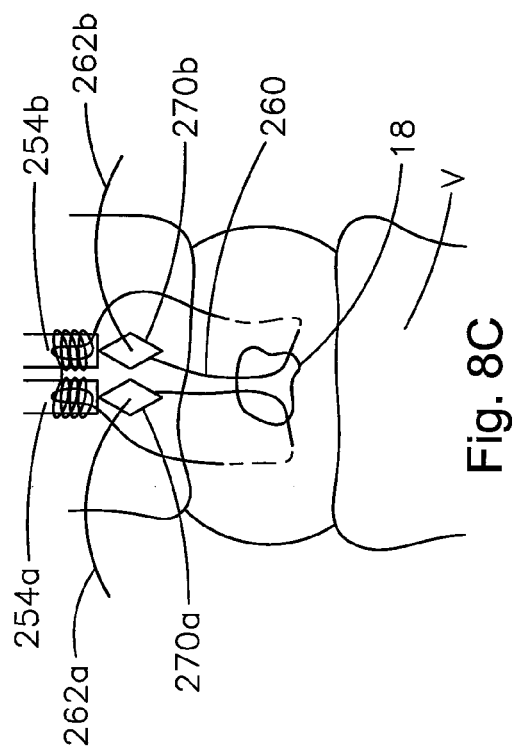
Figure 9B:
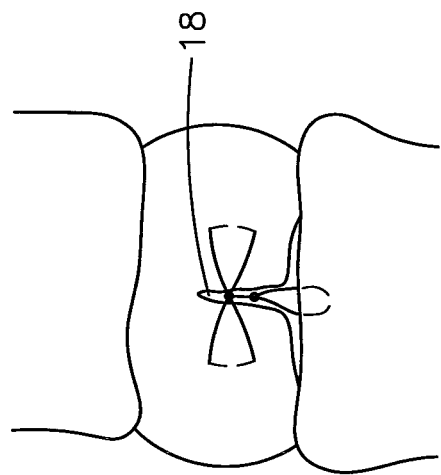
FIGS. 9A-9B are front elevation views of the system shown FIG. 7 repairing a soft tissue defect in accordance with another example method.
Figure 9A:
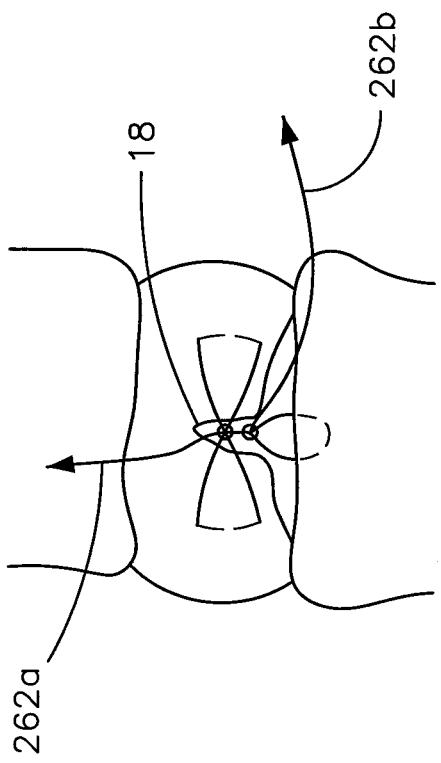

In another embodiment, and in reference to FIG. 7, the soft tissue defect repair system 10 may be configured to place two pre-tied knots proximate to the defect. As shown, the soft tissue repair system 10 may include a suture finishing device 252. As shown, the suture finishing device 252 includes first and second cannulated rods 254a, 254b that may be connected at or near their proximal ends, and first and second suture retrieval devices 258a, 258b translatable within respective channels of the cannulated rods 254a and 254b. The suture finishing device 252 also includes a strand of surgical suture 260 having first and second free ends 262a, 262b and first and second knots 266a, 266b. Similar to the knot 42 of the first embodiment, the first and second knots 266a, 266b are preferably pre-tied threadable knots that can assume the form of a sliding knot, a ratcheting knot, or other various types locking knots known in the field of surgery. The first and second knots 266a, 266b are preferably ratcheting or locking knot configurations to prevent post-operative loosening of the repaired construct. Alternatively the first and second knots 266a, 266b may be made of the same suture and may be connected with a bridging strand of suture. Similar to the cannulated rod 22 of the first embodiment, the first and second cannulated rods 254a, 254b are hollow tubes through which the first and second suture retrieval devices 258a, 258b are passed and over which the first and second knots 266a, 266b are disposed, respectively, and serve as temporary "post strands" to enable the first and second free ends 262a, 262b to pass through the soft tissue 14 on either side of the defect 18. The suture retrieval devices 258a and 258b respectively include first and second knot threaders 270a, 270b, that are preloaded into the first and second cannulated rods 254a, 254b.

In operation, and in reference to FIGS. 7-9B, the first and second cannulated rods 254a, 258b are loaded with the first and second suture retrieval devices 258a, 258b and the first and second knots 266a, 266b are formed around the distal ends of the first and second cannulated rods 254a, 254b. The first and second free ends 262a, 262b are passed through the soft tissue 14 on either side of the defect 18 and then passed back through the first and second cannulated rods 254a, 254b using the first and second suture retrieval devices 258a, 258b. The first and second free ends 262a, 262b can be threaded about the defect 18 in the annulus of the disc and tensioned in a number of different ways, such as threading configuration examples illustrated in FIGS. 8A-8D, and 9A-9B. The defect 18 is then approximated by pulling the first and second free ends 262a, 262b in tension, thereby drawing the first and second cannulated rods 254a, 254b and the first and second knots 266a, 266b to the defect 18. A knot pusher or pair of knot pushers (not shown, but similar to the knot pusher 150) that is preloaded over the first and second cannulated rods 254a, 254b is then implemented to push the first and second knots 266a, 266b off of the first and second cannulated rods 254a, 254b and toward the defect 18 while maintaining the loops of the suture strand 260 in tension. The first and second knots 266a, 266b tighten around the first and second free ends 262a, 262b, thereby allowing the loops of the suture strand 260 to remain secured in the approximated position. Once the first and second knots 266a, 266b are fully tightened in their final position, the first and second free ends 262a, 262b are cut, thereby completing repair of the defect 18. Heat cutting or adhesive application, as described above, may additionally be utilized.

Figure 10:
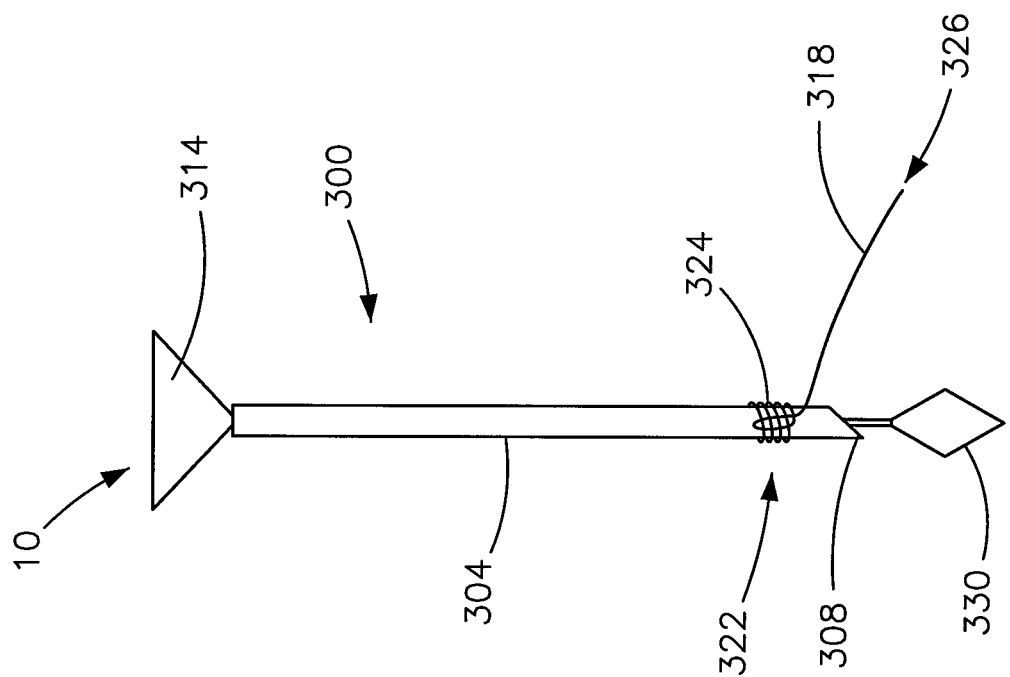
FIG. 10 is a front elevation view of a soft tissue defect repair system in accordance with another embodiment of the present invention.

In another embodiment and in reference to FIG. 10, the soft tissue repair system 10 may also include a cannulated needle having a sharp distal end. As shown, the soft tissue repair system 10 may include a suture finishing device 300 configured to puncture tissue 14. In that regard the suture finishing device 300 includes a longitudinally extending cannulated rod 304 having a sharp distal end 308. Other than the sharp distal end 308, cannulated rod 304 includes similar features, and functions in a similar manner as the cannulated rod 22 described in reference to FIGS. 1-3C. Therefore, suture finishing device 300 also includes a suture retrieval device 314 that is translatable within a channel that extends through the cannulated rod 304. As shown, the suture finishing device 300 also includes a strand of suture 318 having a knot 322 (e.g. a pre-tied knot) tied about a target knot location 324 of the cannulated rod 304, and a first free end 326 that may be configured to be attached to a needle. The distal end of the suture retrieval device 314 includes a threader 330 for capturing the first free end 326 of the suture strand 318.

Figure 11:
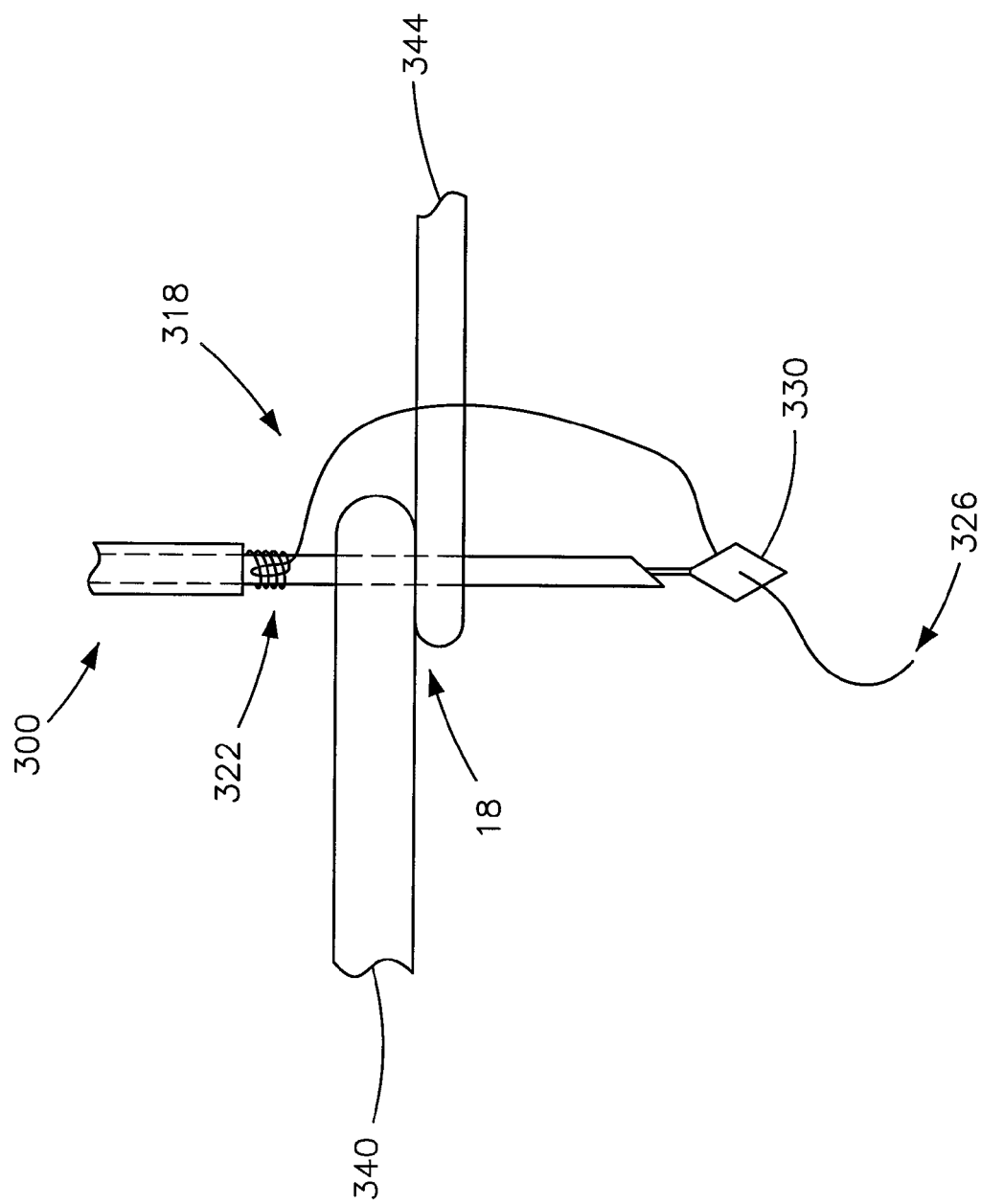
FIG. 11 is a front elevation view of the system shown in FIG. 10 repairing a soft tissue defect in accordance with an example method.

In operation, and in reference to FIGS. 11, and 12A-12E, the soft tissue defect repair device 300 is configured to approximate defects 18 of the type in which simple attachment of a first piece of tissue 340 overlying a second piece of tissue 344 is desired, as is illustrated in FIG. 11, but is also applicable for non-overlying tissue repair, as is illustrated in FIGS. 12A-12E.

Figure 12C:
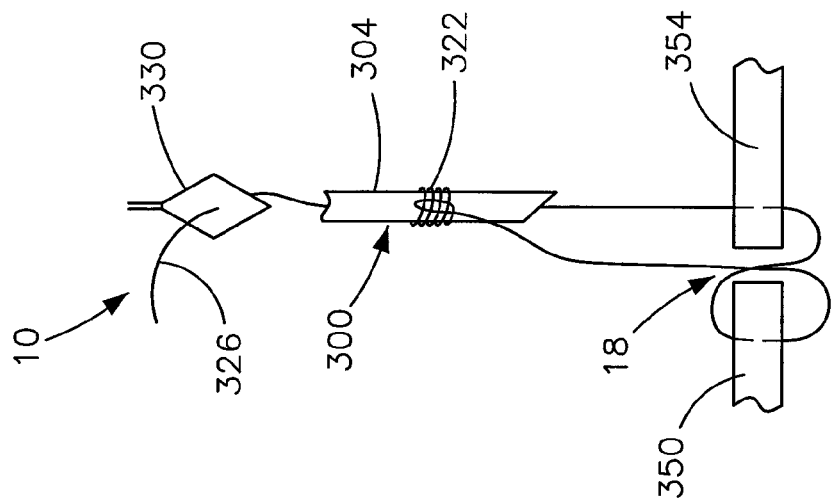
FIGS. 12A-12E illustrate front elevation views of the system shown FIG. 10 repairing a soft tissue defect in accordance with another example method.
Figure 12B:
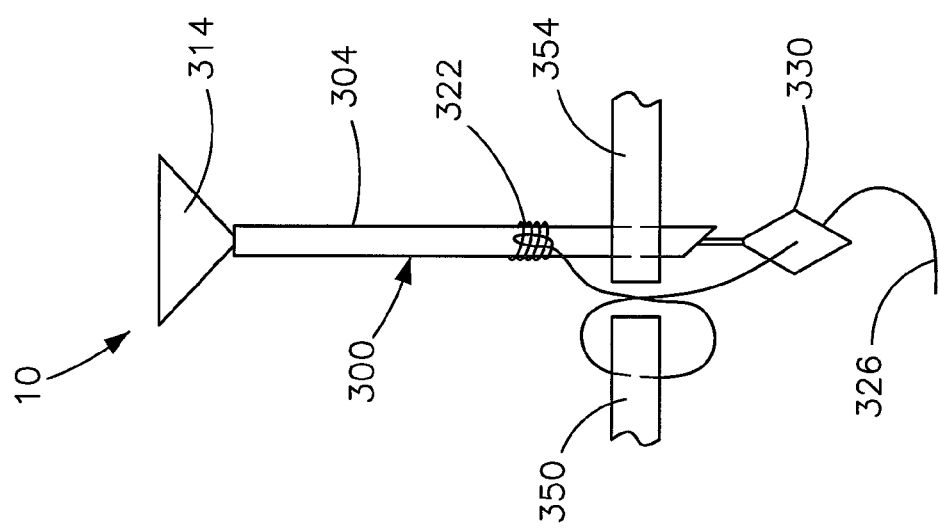
Figure 12A:
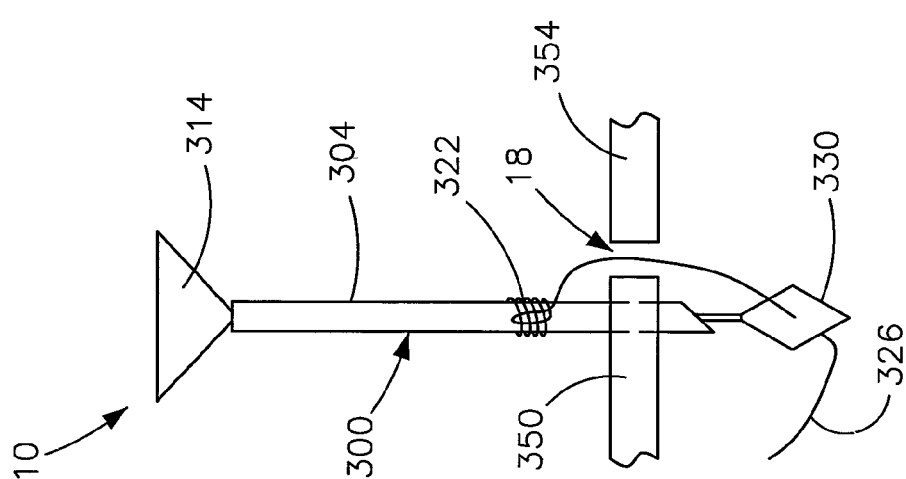
Figure 12E:
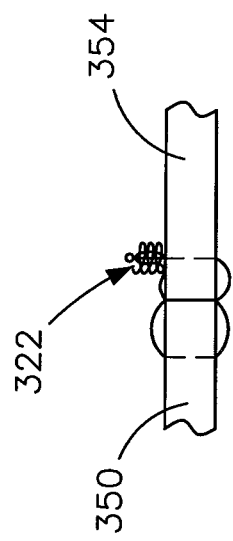
Figure 12D:
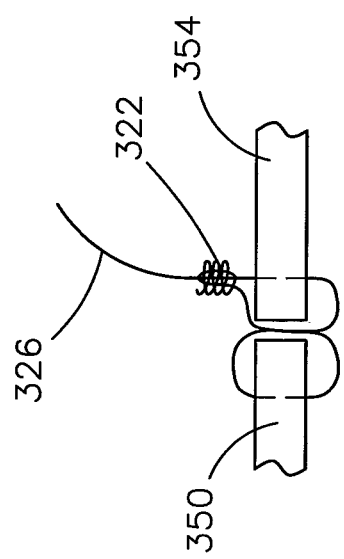

If the system is to be used for non-overlying tissue repair as shown in FIGS. 12A-12E the soft tissue repair system may first be inserted through a first piece of tissue 350, as shown in FIG. 12A. Once through the first piece of tissue 350, the suture retrieval device 314 may temporarily capture the first free end 326 of the suture strand 318 to pass the suture through the tissue. The suture can then be released and the soft tissue repair system may then be passed through a second piece of tissue 354, and the suture can be recaptured by suture retrieval device 314, as shown in FIG. 12B to thereby create a stitch on each side of the tissue. Once the stitch has been placed around defect 18 the suture retrieval device 314 may then be pulled through the cannulated rod 304, as shown in FIG. 12C. The knot 322 may then be slid off of the distal end of the cannulated rod 304 and positioned proximate to the defect 18 as shown in FIGS. 12D and 12E.

In accordance with another embodiment, and in reference to FIGS. 13A-13G, the soft tissue defect repair system 10 may also be configured to have suture passing capabilities. As shown in FIGS. 13A-13G, the soft tissue defect repair system 10 includes a suture finishing device 402 incorporated into a suture passing device 408, which may further simplify the system to thereby allow for a quicker annulus closure solution. In that regard, the soft tissue defect repair system 10 of FIGS. 13A-13G includes a cannulated rod 410 (e.g. a body member having a longitudinal channel), a boom arm 414 extending distally from a distal end of the cannulated rod 410, and a boom arm housing 418 defined in a distal portion of the boom arm 414. A tissue receiving gap 422 is defined between the distal end of the cannulated rod 410 and the boom arm housing 418. The soft tissue repair system 10 of FIGS. 13A-13G also includes a needle 430, and a shuttling element 434 detachably coupleable to both the needle 430 and the boom arm housing 418. The needle 430 is reciprocally translatable within the cannulated rod 410 between an extended position, in which the needle 430 engages a bore 436 defined by the boom arm housing 418, and a retracted position in which the needle 430 is disengaged from the boom arm housing 418.

The soft tissue repair system 10 of FIGS. 13A-13G also includes, a strand of suture 440 having knot 444 (e.g. a pre-tied knot) tied about a target knot location 446 of the cannulated rod 410 and a first free end 448 attached to the shuttling element 434. The knot 444 is preferably similar to the previously described threadable ratcheting or locking knots. The cannulated rod 410 is aligned with the boom arm housing 418 and is configured such that downward displacement of the needle 430 with respect to the cannulated rod 410 brings about an engagement of the distal tip of the needle 430 with respect to the boom arm housing 418 in such a way that the shuttling element 434 coupled to the distal end of the needle 430 is captured by the boom arm housing 418.

The shuttling element 434 and needle 430 may include corresponding engagement features that allow the shuttling element 434 to be detachably coupled to the needle 430. For example, the needle 430 and the shuttling element 434 may include corresponding threads configured to allow the shuttling element 434 to be detachably coupled to a distal end of the needle 430 about an external surface of the needle 430. Alternatively, the threads may be configured to allow the shuttling element 434 to be detachably coupled within a channel of the needle 430. Similarly, the shuttling element 434 may include a locking mechanism that is configured to engage a locking interface defined by the boom arm housing 418 to allow the shuttling element 434 to be detachably coupled to the boom arm housing 418. For example, the locking mechanism and locking interface may be corresponding threads configured to allow the shuttling element 434 to be detachably coupled to the boom arm housing 418. The engagement feature, the locking mechanism, and the locking interface have been described in accordance with two embodiments, and it should be appreciated that they can be constructed in accordance with alternative embodiments. For instance, the engagement feature, locking mechanism, and locking interface can be constructed as described in U.S. patent application Ser. No. 12/693,820, filed on Jan. 26, 2010, the contents of which are incorporated by reference in their entirety.

Figure 13A:
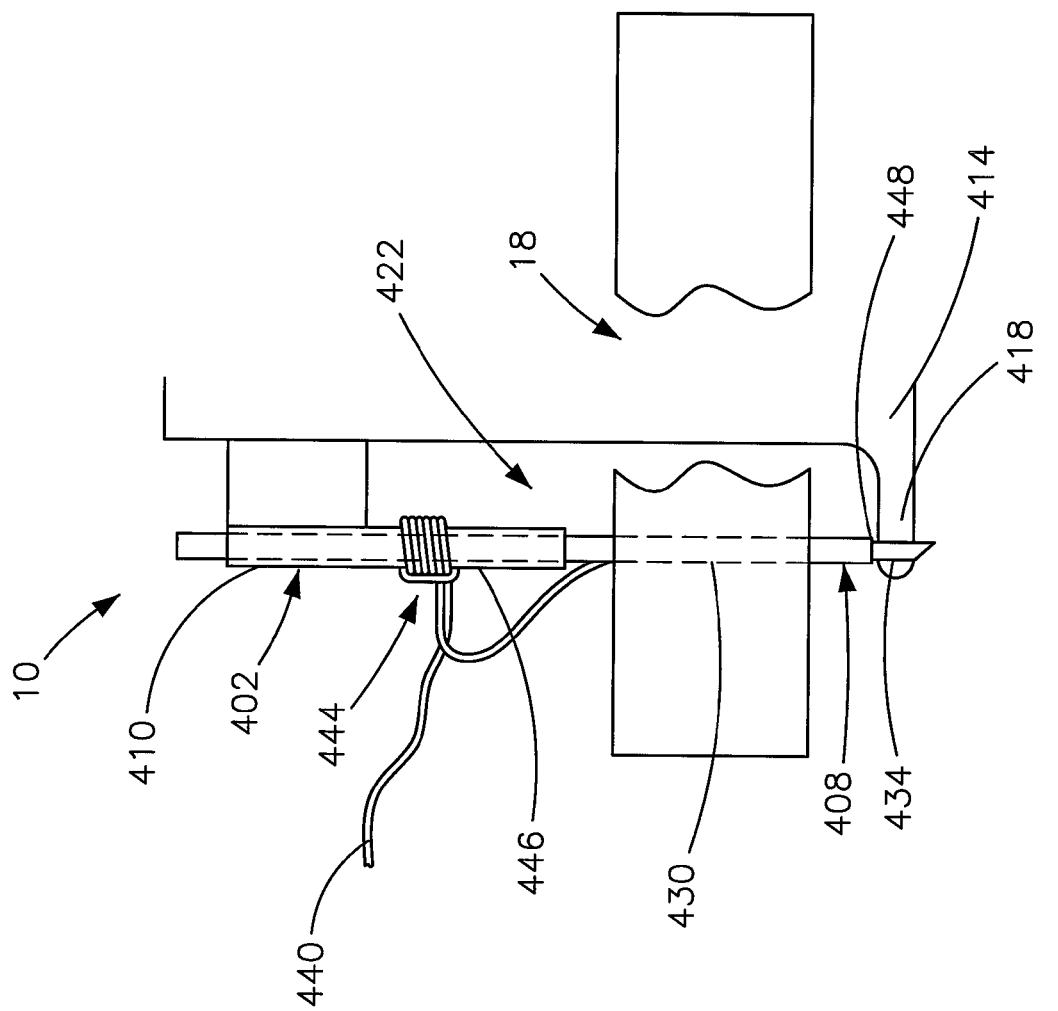
FIG. 13A is a cross-sectional view of another embodiment of a soft tissue defect repair system of the present invention, wherein the soft tissue repair system is partially positioned within a defect in an annulus in a first repair step.
Figure 13B:
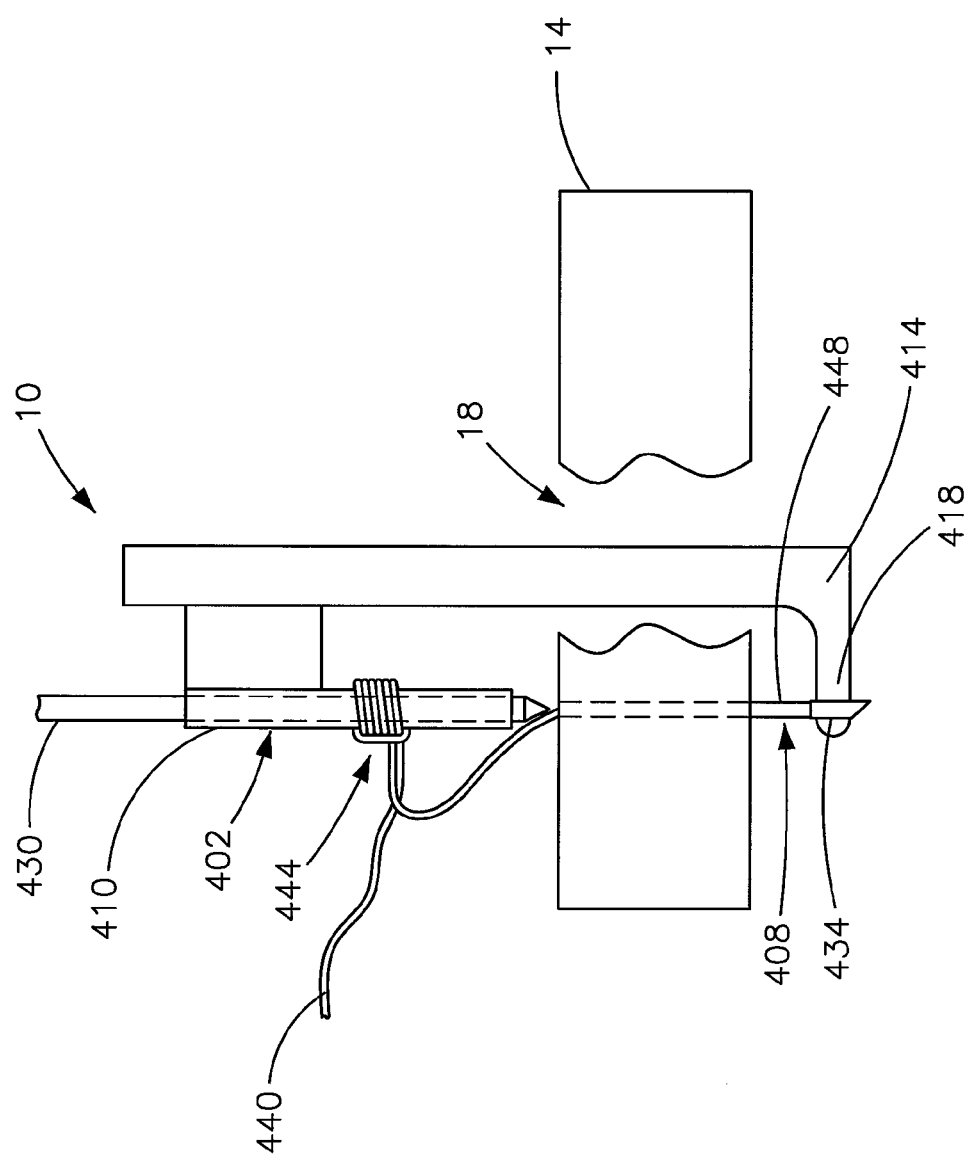
FIG. 13B is a cross-sectional view of the soft tissue defect repair system of FIG. 13A, showing a second step of using the soft tissue defect repair system.

In operation, and in continuing reference to FIGS. 13A-13G, the knot 444 is pre-tied around the target knot location 446 of the cannulated rod 410 and the needle 430 is inserted through the cannulated rod 410. The shuttling element 434 is detachably coupled to the distal end of the needle 430. The boom arm housing 418 is placed through the defect 18 in the soft tissue 14, preferably an annulus of a disc. In the case in which the soft tissue 14 is an intervertebral disc annulus, the boom arm housing 418 is placed through the defect 18 and into the interior of the disc space, i.e., past the annulus tissue and into the nucleus pulposus tissue. The needle 430 is advanced distally with respect to the cannulated rod 410 such that the distal tip of the needle 430, and the shuttling element 434 attached thereto pass through the soft tissue 14 and engage the boom arm housing 418, as shown in FIG. 13A. An actuator may be employed to cause the shuttling element 434 to detachably couple to the boom arm housing 418 and detach from the needle 430. The needle 430 may then be retracted back through the soft tissue 14 and into the cannulated rod 410 while the shuttling element 434 with the first free end 448 of the suture strand 440 attached thereto remains coupled to the boom arm housing 418, as shown in FIG. 13B.

Figure 13C:
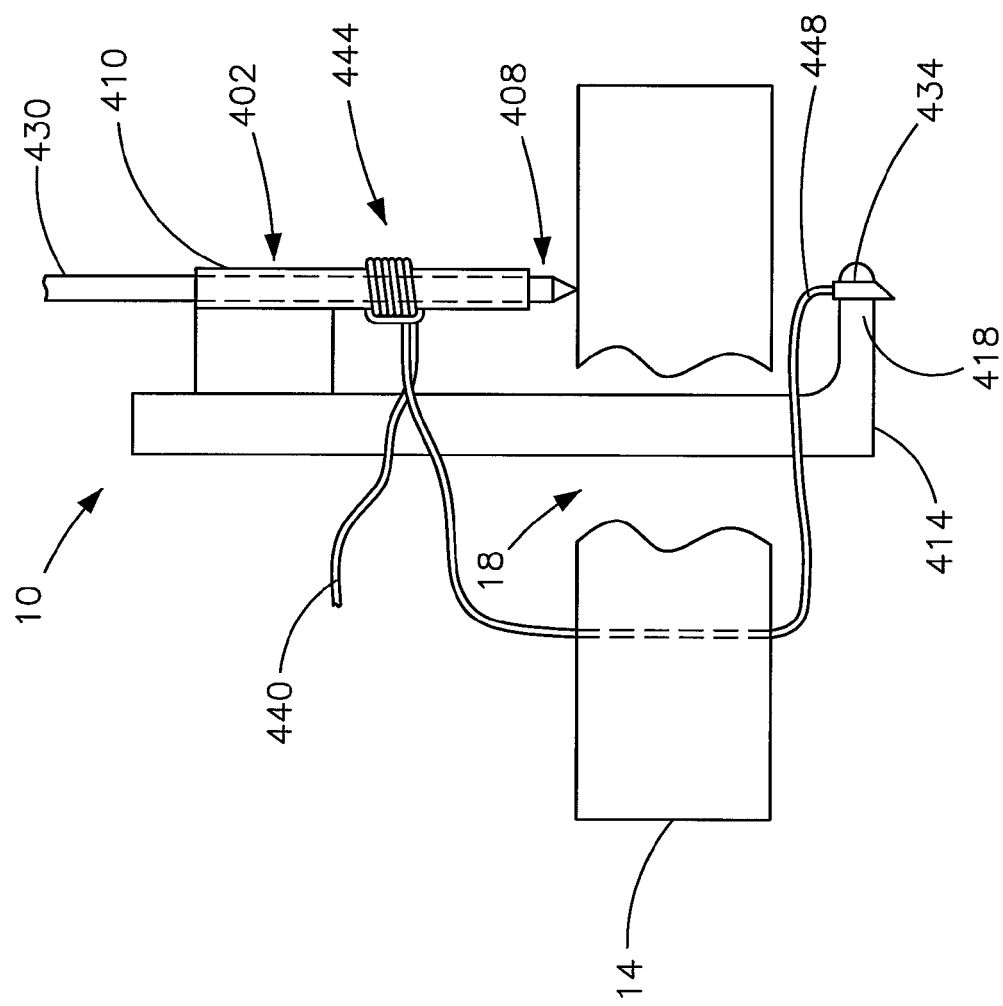
FIG. 13C is a cross-sectional view of the soft tissue defect repair system of FIG. 13B, showing a third step of using the soft tissue defect repair system.
Figure 13D:
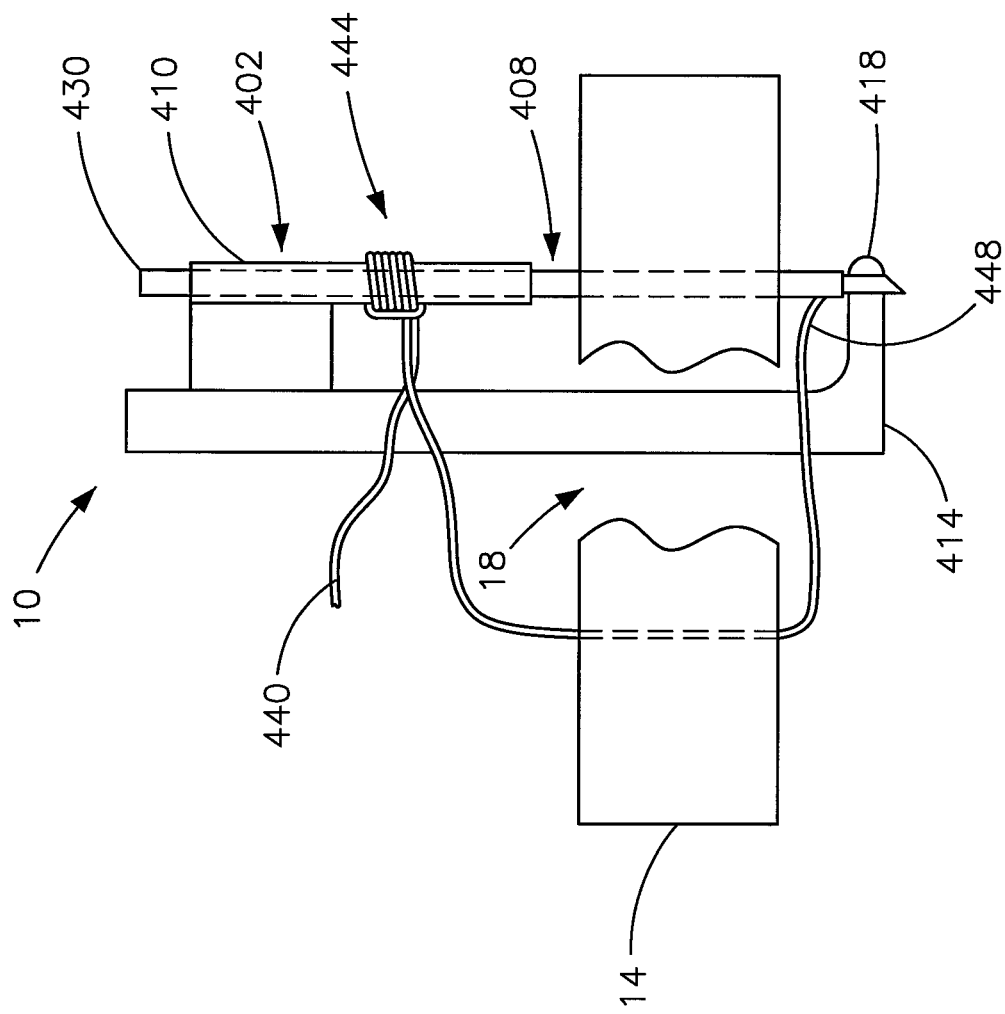
FIG. 13D is a cross-sectional view of the soft tissue defect repair system of FIG. 13C, showing a fourth step of using the soft tissue defect repair system.
Figure 13E:
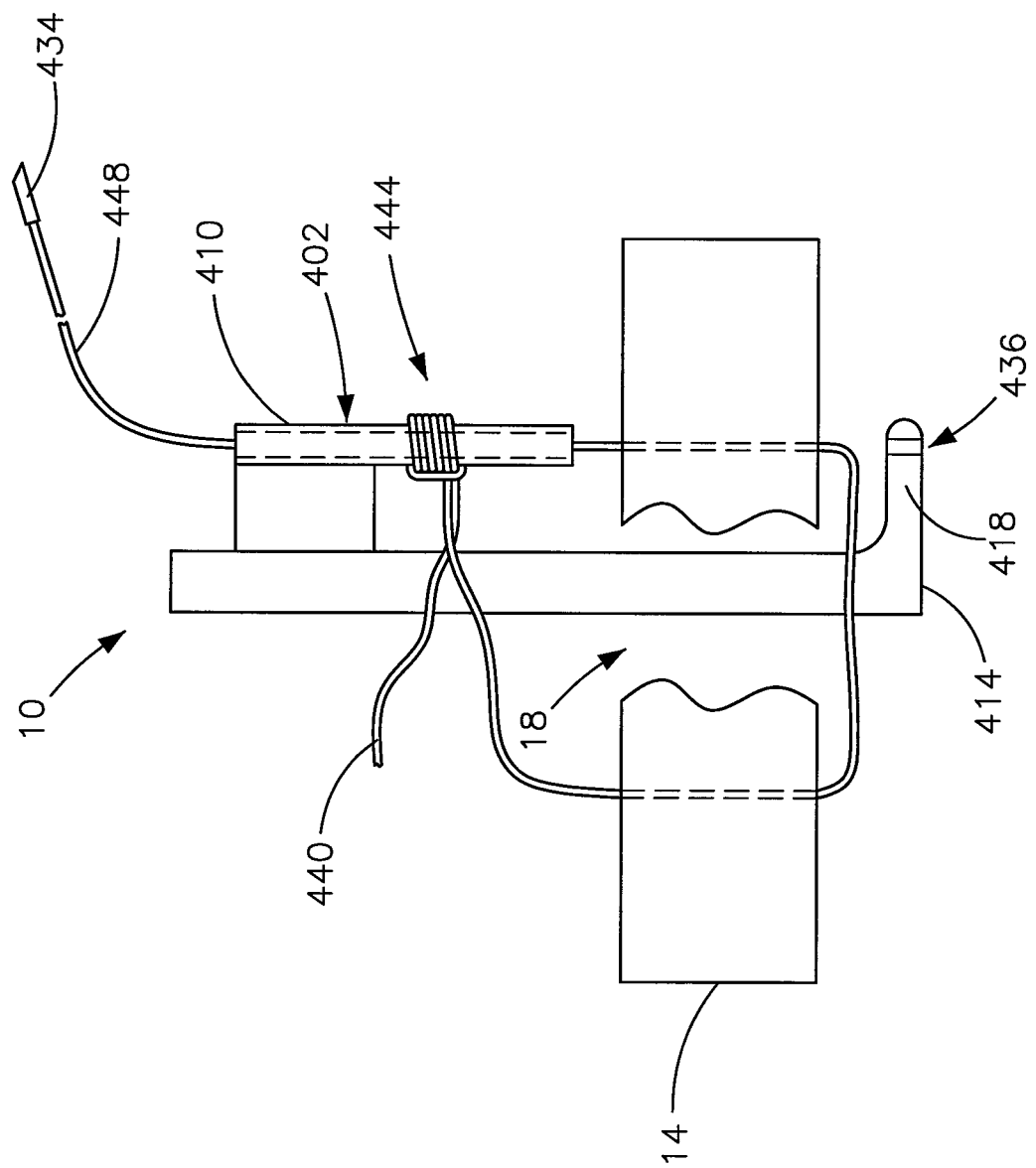
FIG. 13E is a cross-sectional view of the soft tissue defect repair system of FIG. 13D, showing a fifth step of using the soft tissue defect repair system.

The soft tissue defect repair system 10 is then rotated to another location in the tissue adjacent to the defect, for example, approximately one hundred eighty degrees (180°), such that the needle 430 is disposed above the opposite side of the defect 18 and the boom arm housing 418 and the shuttling element 434 are disposed below the opposite side of the defect 18 and aligned directly below the needle 430, as shown in FIG. 13C. The needle 430 is then advanced distally with respect to the cannulated rod 410 such that the distal tip of the needle 430 passes through the soft tissue 14 and engages the shuttling element 434 coupled to the boom arm housing 418. The actuator may be once again employed to re-couple the needle 430 to the shuttling element 434, and decouple the shuttling element 434 from the boom arm housing 418, as shown in FIG. 13D. In this regard, the soft tissue defect repair system 10 of FIGS. 13A-13G has bi-directional suture passing capabilities. The needle 430 and the shuttling element 434 are then retracted back through the soft tissue 14 and into the channel of the cannulated rod 410, as shown in FIG. 13E. This process can be repeated to accommodate a number of different suture passing configurations, such as those shown in FIGS. 16A-16J and described in reference to these figures below. It should be appreciated that the procedure may begin with the shuttling element 434 initially attached to the boom arm housing 418 (resulting in a knot on the interior of the tissue defect).

Once the suture 440 has been passed in the desired configuration, the needle 430 and the shuttling element 434 are retracted back into and out through the proximal end of the cannulated rod 410, as shown in FIG. 13F. As shown, the first free end 448, now protruding from the proximal end of the cannulated rod 410, is grasped and the knot 444 is pushed off of the distal end of the cannulated rod 410, preferably using a knot pusher as previously described, to push the knot 444 off of the cannulated rod 410 to the defect 18, as shown in FIG. 13G. The soft tissue repair system 10 is then removed and the steps can be performed one or more additional times with one or more additional soft tissue repair systems if additional sutures are desired to approximate the defect 18. The one or more suture strands are then drawn tight by pulling the first free end(s) attached to the shuttling element(s) 434 into tension to tighten the knot(s) 444 around the first free end(s) 448 and thereby approximate the defect 18. The tensioning of the suture strand 440 to approximate the defect 18 can be accomplished by using a knot pusher as described above, or by incorporating a ratcheting trigger mechanism into the soft tissue repair system 10 that functions to draw the knot 444 to the defect 18. Once the knot 444 is fully tightened and the defect 18 is approximated, the first free end 448 (or ends) is trimmed. Heat cutting or adhesive application, as discussed above, may additionally be applied.

Figure 14A:
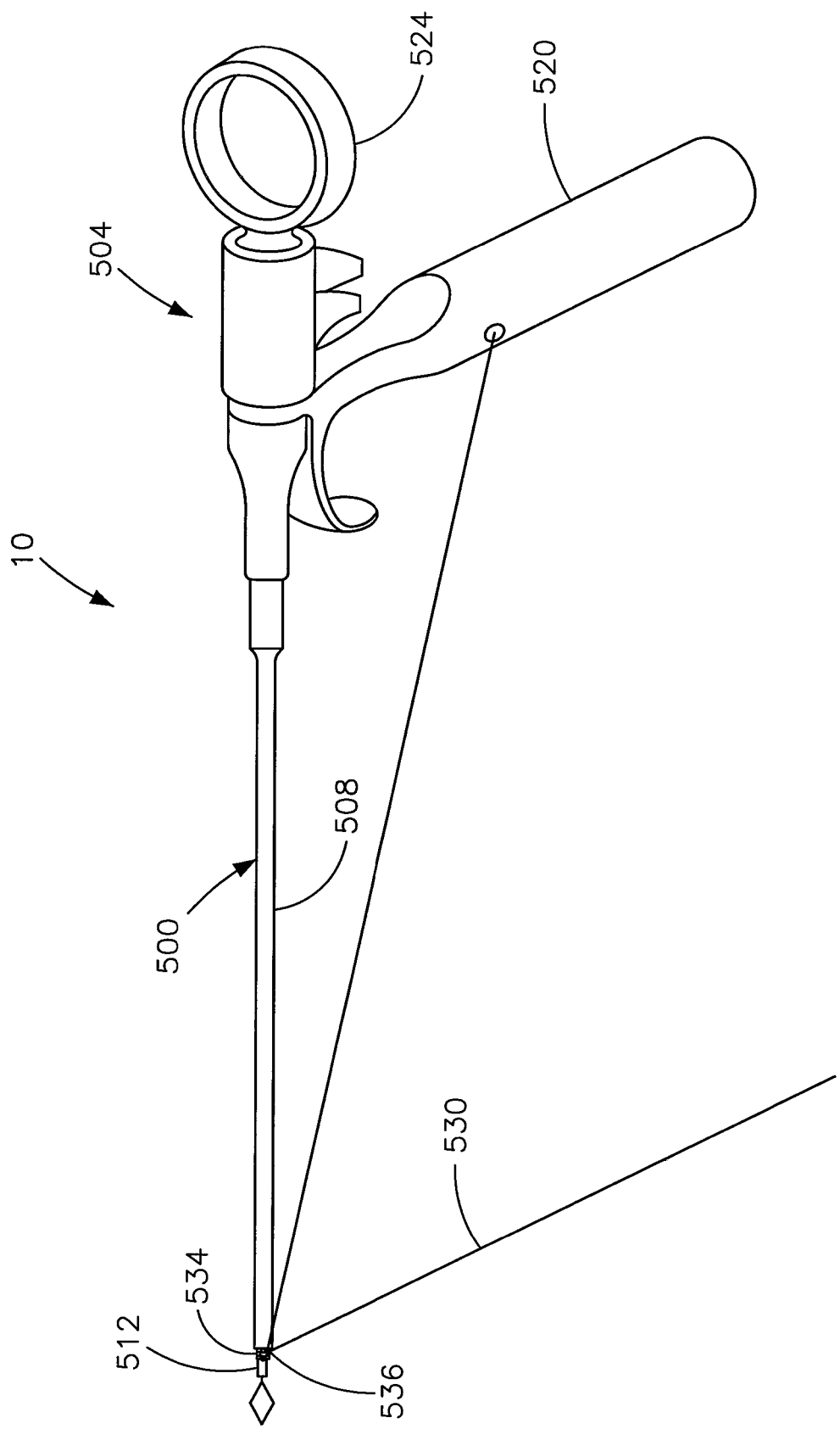
FIG. 14A is a perspective view of another embodiment of a soft tissue defect repair system of the present invention.
Figure 14B:
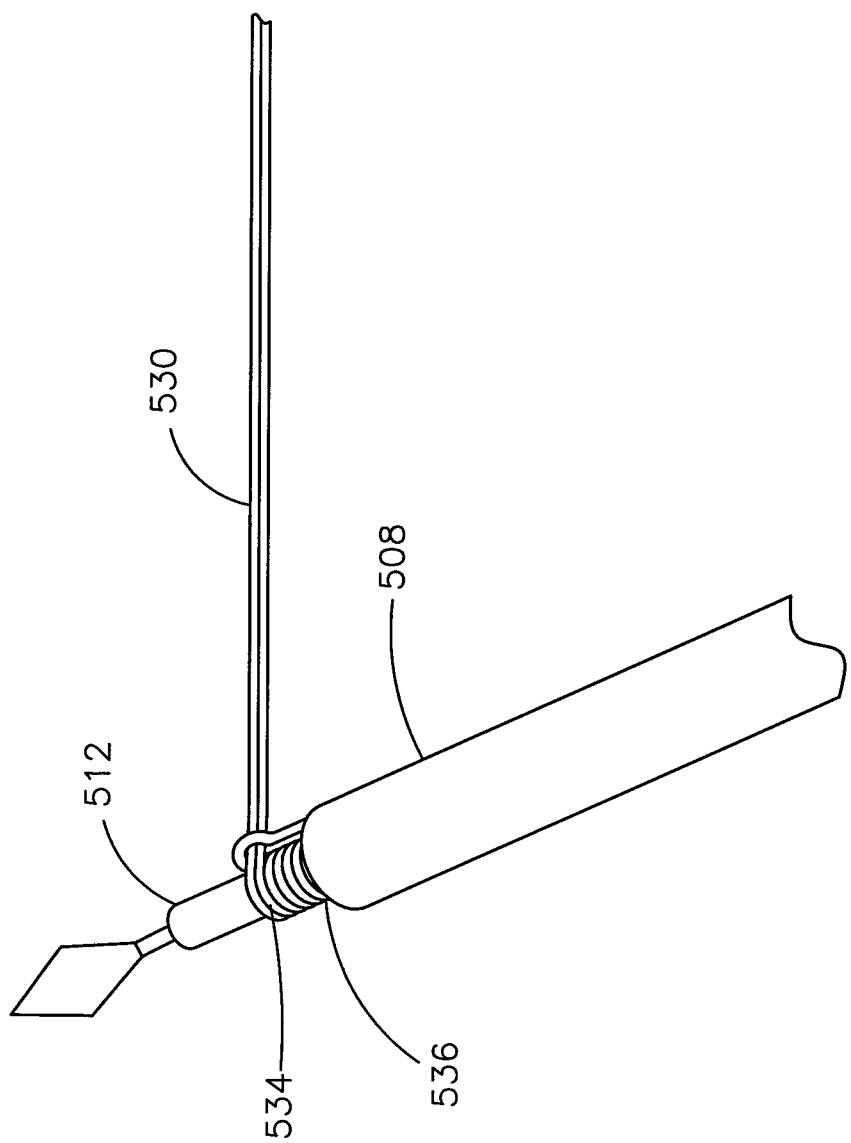
FIG. 14B is an expanded view of a distal end of the soft tissue repair defect repair system shown in FIG. 14A.
Figure 14C:
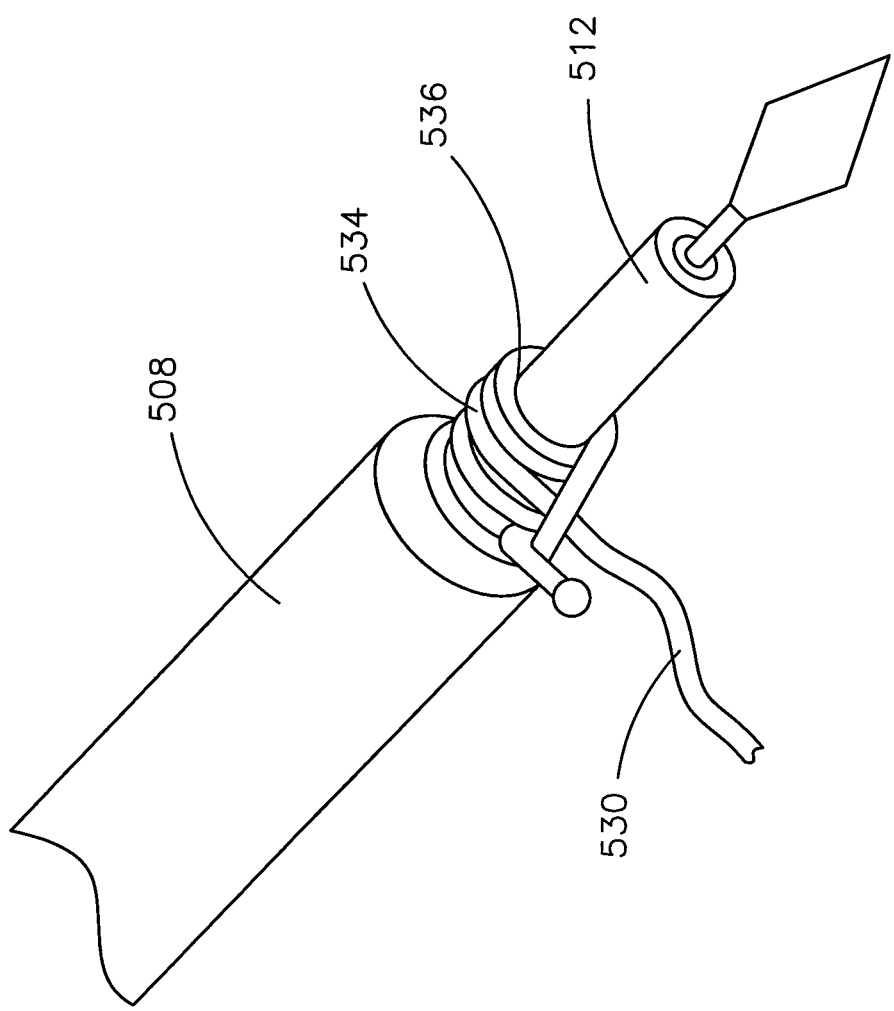
FIG. 14C is an alternative knot arrangement that may be used with the soft tissue defect repair system shown in FIG. 14A.

In reference to FIGS. 14A-14C, the soft tissue repair system may include other features and configurations. For example, as shown in FIG. 14A, the soft tissue repair system 10 may include a suture finishing device 500. The suture finishing device 500 includes a body portion 504, a knot pusher 508 extending distally from the body portion 504, and a cannulated rod 512 extending through a channel of the knot pusher 508 and out a distal end of the knot pusher 508. The device 500 may also include a handle 520 extending down from the body portion 504, and a second handle 524 extending proximally from the body portion 504. The handle 520 may be configured to enable an individual to securely hold the device 500, while handle 524 may be ring shaped to allow a user to pull the handle 524 proximally with respect to the body portion 504. Like handle 58 of the first embodiment, handle 524 is coupled to a suture retrieval device, so as the handle 524 is pulled proximally, the suture retrieval device is also pulled proximally.

As shown in FIGS. 14A and 14B, the device 500 also includes a suture strand 530 having a knot 534 (e.g. a pre-tied knot) tied about a target knot location 536 of the cannulated rod 512. As shown in FIGS. 14A and 14B, the knot 534 may be tied such that both ends of the suture strand 530 extend away from the instrument. It should be understood, however, that one end of the strand may be connected to the first free end of the suture, while the other end of the strand is attached to the device 500, as shown in FIG. 14A, or manipulated into a heat cut ball, as shown in FIG. 14C.

The pre-tied knot 534 shown in FIG. 14B may be made by first making five loops around the rod 512 in a clockwise motion using the first free end. Any slack from the five suture lops may be removed by sliding the loops proximally and by applying tension to the first and second free ends. Next, a sixth loop may be made by loosely wrapping the first free end around the rod 512, above (distal) the first loop such that the first free end crosses above the second free end and around the rod 512 to create a gap. The first free end may then be routed through the gap on its return from being wrapped around the rod 512. At this point the second free end should be pulled perpendicular to the rod 512, and when the first free end is pulled taught the knot may be completed.

The pre-tied knot 534 shown in FIG. 14C may be made by making a first loop around the rod 512, a second loop above (distal) the first loop, and a third loop below (proximal) the first loop to thereby create a first gap between the rod 512 and the suture. The third loop may be completed by continuing to wrap the loop around the rod 512 and through the first loop gap. A fourth loop may then be positioned below (proximal) the third loop such that a second gap is created and the second free end is passed through the second gap when the fourth loop is completed. At this point, the slack from the four loops may be removed by sliding the loops proximally, and by applying tension to the first and second free ends. When the first and second free ends may be pulled taut, the knot may be completed. As shown, the second free end may be formed into a ball.

Figure 15:
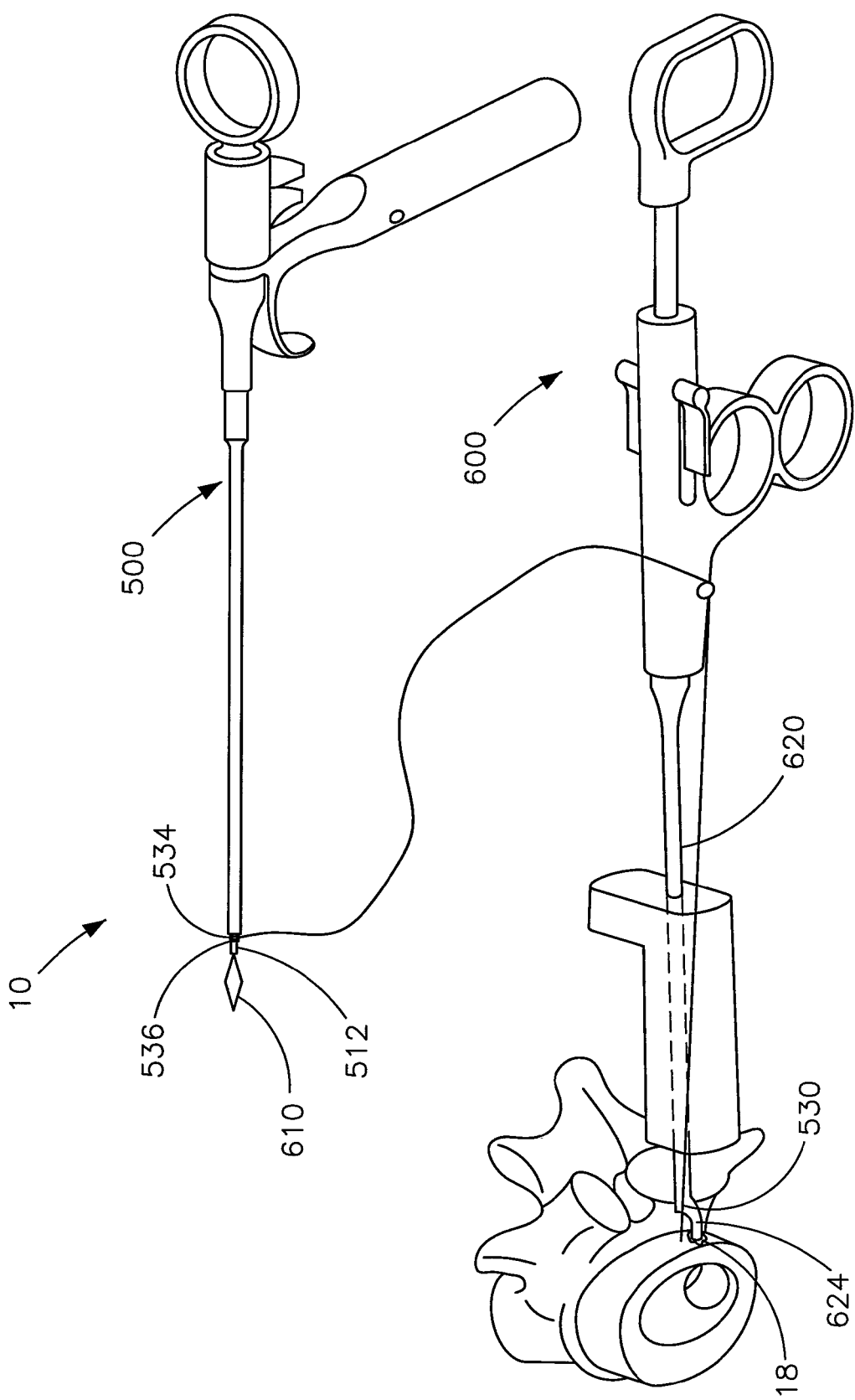
FIG. 15 is the soft tissue defect repair system of FIG. 14A tethered to a bi-directional suture passing instrument.

As shown in FIG. 15, the soft tissue repair system 10 may include the suture finishing device 500 tethered to a separate suture passing instrument 600 (e.g. a bi-directional suture passing instrument). The suture passing instrument 600 may include any of the configurations and/or structures disclosed in U.S. patent application Ser. No. 12/693,820. For example, the suture passing instrument 600 may include a body member 620 and a boom arm 624 extending distally from the body member 620. Though not shown, the boom arm 624 includes a boom arm housing at its distal end for selectively housing a shuttling element. The instrument 600 also includes a needle having the shuttling element detachably coupled thereto, that is reciprocally translatable within a channel defined by the body member 620 between an extended position in which the needle engages a boom arm housing defined by a distal end of the boom arm 624 and a retracted position in which the needle is disengaged from the boom arm housing 624. Generally, the suture passing instrument 600 operates and functions similar to the system disclosed in reference to FIGS. 13A-13G.

In operation, the suture passing instrument 600 will approximate the defect 18 by passing the needle having the shuttling element detachably coupled to its distal end through a piece of tissue. As with the embodiment shown in FIGS. 13A-13G the first free end of the suture strand 530 is attached to the shuttling element of the suture passing instrument 600. However, the knot 534 of the suture strand 530 is disposed about the cannulated rod 512 of the suture finishing device 500. In this regard the suture passing device 600 is tethered to the suture finishing device 500. Once the stitch has been placed around defect 18, the shuttling element may be removed and the first free end may be captured by a suture retrieval device 610 extending out from the cannulated rod 512 of the suture finishing device 500. The suture retrieval device 610 may then be drawn into the cannulated rod 512, and the knot 534 may be pushed off of the distal end of the cannulated rod 512 toward the defect 18 by tensioning the first free end of the suture to thereby finish the procedure.

In reference to FIGS. 16A-16J, various suture passing configurations are illustrated that can be practiced using the various soft tissue defect repair systems disclosed herein, or can be accomplished using hand suturing techniques. While the suture passing techniques are described in reference to a fissure or other defect inherent to the annulus fibrosus tissue of the intervertebral disc, which is located between adjacent vertebrae V, it is envisioned that the suture passing configurations described herein are applicable to a range of other soft tissue defects, such as abdominal wall herniations, rotator cuff tears in the shoulder, and meniscal tears in the knee.

Figure 16A:
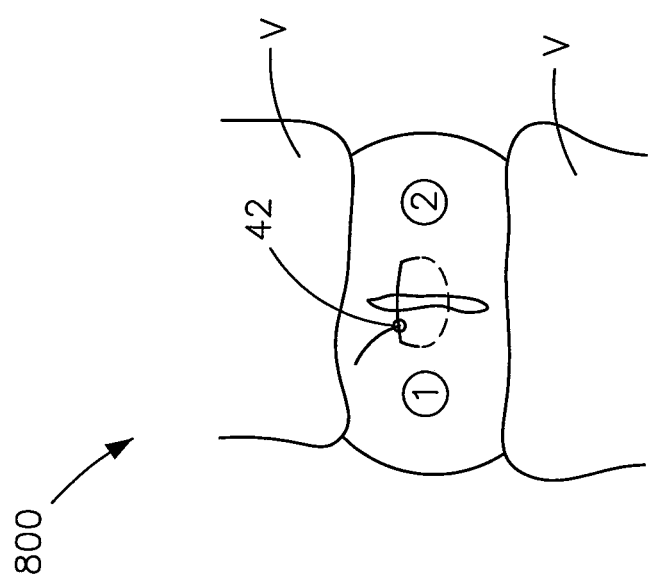
FIG. 16A is a front elevation view of a simple stitch.
Figure 16B:
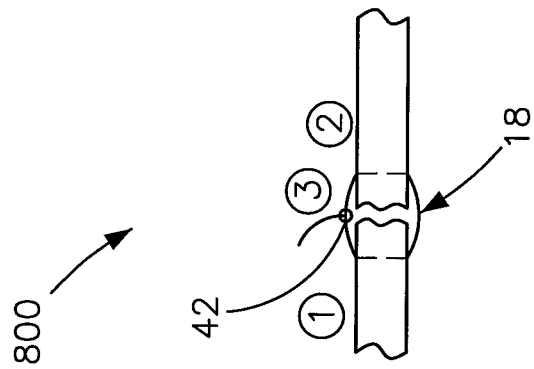
FIG. 16B is a side view of the simple stitch shown in FIG. 16A.

In reference to FIGS. 16A and 16B, a simple stitch suture passing method 800 is illustrated, in which the suture is passed from the exterior of the disc D through the annulus and into the interior of the disc space on a first side of the defect 18, then passed horizontally through the interior of the annulus and under the defect 18, and then retrieved from the interior to the exterior of the annulus on the second, opposite side of the defect 18. The first free end of the suture strand is passed through the preloaded knot housed on the cannulated rod and the knot is pushed toward the defect 18 (instrumentation is removed for clarity). The first free end is drawn taught, and the defect 18 is approximated with the knot coming to rest on the exterior of the defect 18. Alternately, the first free end may first be passed from the interior to the exterior of the annulus on a first side of the defect 18, then horizontally over the exterior of the defect 18, passed from the exterior to the interior of the annulus on the second, opposite side of the defect 18, resulting in the knot 42 being retained on the interior of the approximated defect 18 and in a generally zero profile construct. In general, any stitch configurations that results in the knot 42 being retained interior to the disc can incorporate the knot pusher to insert the knot 42 through the defect 18.

Figure 16C:
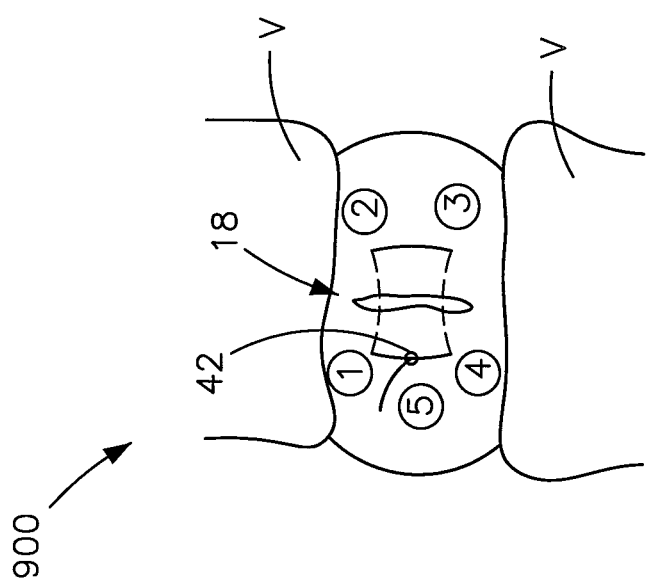
FIG. 16C is a front elevation view of a horizontal box mattress stitch.

In reference to FIG. 16C, a horizontal box mattress stitch suture passing method 900 is illustrated, in which a pair of mattress stitches are placed on either side of the defect 18 through the full thickness of tissue to be approximated. The first free end of the suture strand is passed from the exterior of the annulus to the interior of the annulus on a first side of the defect 18, passed horizontally under the defect 18 to the second, opposite side of the defect 18, retrieved from the interior to the exterior of the annulus on the second, opposite side of the defect 18, passed vertically (e.g. caudally) on the exterior of the annulus on the second, opposite side of the defect, passed from the exterior of the annulus to the interior of the annulus on the second, opposite side of the defect 18, passed horizontally under the defect 18 back to the first side of the defect 18, and then retrieved from the interior to the exterior of the annulus on the first side of the defect 18 and then passed through a knot 42. The tissue is then approximated by deploying the knot 42 as described above, with the knot 42 being retained on the exterior of the defect 18. Alternately, the first free end may first be passed from the interior to the exterior of the annulus on a first side of the defect 18, then horizontally over the exterior of the defect 18, passed from the exterior to the interior of the annulus on the second, opposite side of the defect 18, passed vertically (e.g. caudally) on the interior of the annulus on the second, opposite side of the defect, passed from the interior of the annulus to the exterior of the annulus on the second, opposite side of the defect 18, passed horizontally over the defect 18 back to the first side of the defect 18, and then passed from the exterior to the interior of the annulus on the first side of the defect 18 and then passed through a knot 42, resulting in the knot 42 being retained on the interior of the approximated defect 18 and in a generally zero profile construct.

Figure 16D:
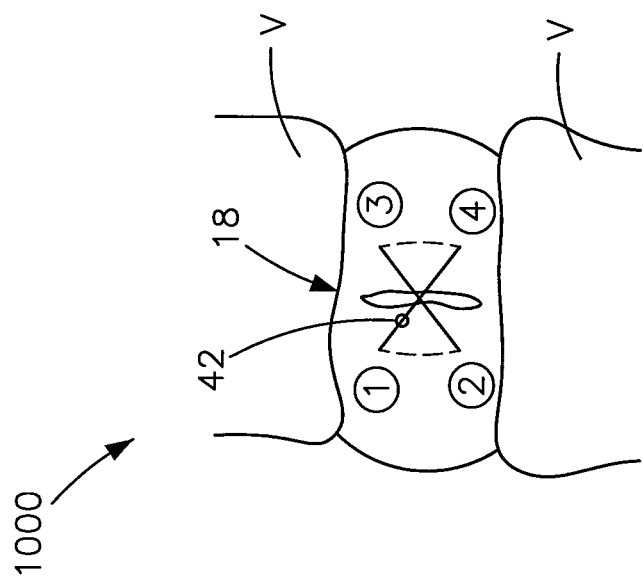
FIG. 16D is a front elevation view of a horizontal criss-cross mattress stitch.

In reference to FIG. 16D, a horizontal criss-cross mattress stitch suture passing method 1000 is illustrated, in which the first free end of the suture strand is passed from the exterior to the interior of the annulus on the first side of the defect 18, then passed vertically (e.g. caudally) on the first side of the defect 18, then retrieved from the interior to the exterior of the annulus on the first side of the defect 18, then passed diagonally (e.g. caudal to cranial) over the exterior of the defect 18 to the second, opposite side, then passed from the exterior to the interior of the annulus on the second, opposite side of the defect 18, then passed vertically (e.g. caudally) on the interior of the annulus on the second, opposite side of the defect 18, then retrieved from the interior to the exterior of the annulus on the second, opposite side of the defect 18, then passed through a knot 42. The tissue is then approximated by deploying the knot 42 as described above, with the knot 42 being retained on the exterior of the defect 18.

Figure 16F:
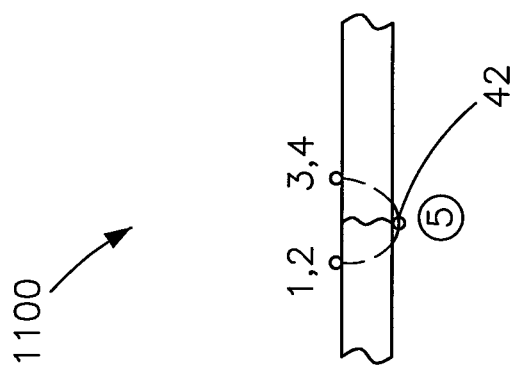
FIG. 16F is a side view of the inverted horizontal criss-cross mattress stitch shown in FIG. 16E.
Figure 16E:
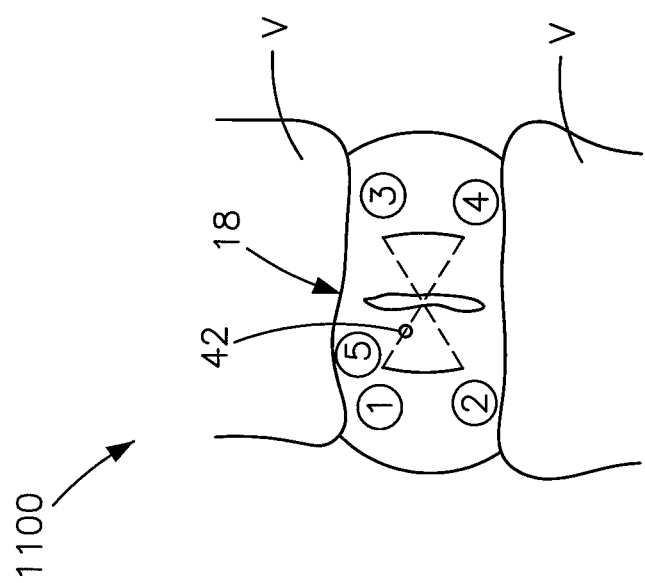
FIG. 16E is a front elevation view of an inverted horizontal criss-cross mattress stitch.

In reference to FIGS. 16E and 16F, an inverse horizontal mattress stitch suture passing method 1100 is illustrated that is similar to the horizontal criss-cross mattress stitch suture passing method 1000 illustrated in FIG. 16D with the exception that the sequence of suture passing direction is reversed (exterior-to-interior becomes interior-to-exterior) to retain the knot 42 on the interior of the annulus.

Figure 16G:
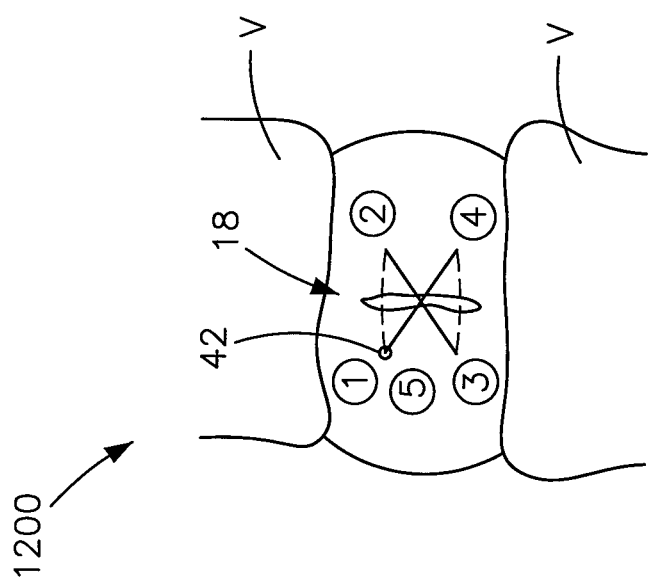
FIG. 16G is a front elevation view of a vertical mattress stitch.

In reference to FIG. 16G, a vertical mattress stitch suture passing method 1200 is illustrated, in which the first free end of the suture strand is passed from the exterior to the interior of the annulus on the first side of the defect 18, then passed horizontally under the defect 18 to the second, opposite side of the defect 18, then retrieved from the interior to the exterior of the annulus on the second, opposite side of the defect 18, then passed diagonally over the exterior of the defect 18 to the first side of the defect 18, then passed from the exterior to the interior of the annulus on the first side of the defect 18, then passed horizontally under the defect to the second, opposite side of the defect 18, then retrieved from the interior to the exterior of the annulus on the second, opposite side of the defect 18, and passed through the knot 42. The knot 42 is then drawn to the defect and is retained on the exterior of the defect 18.

Figure 16I:
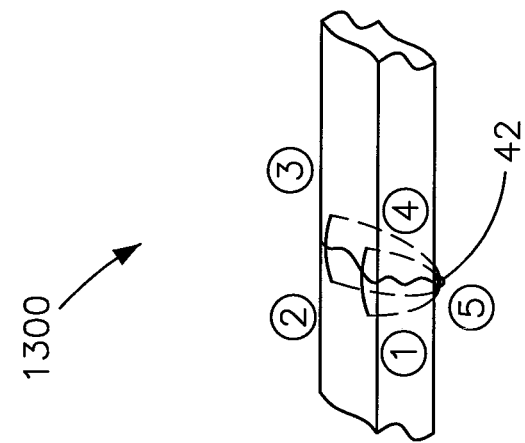
FIG. 16I a side view of the inverted vertical mattress stitch of FIG. 16H.
Figure 16H:
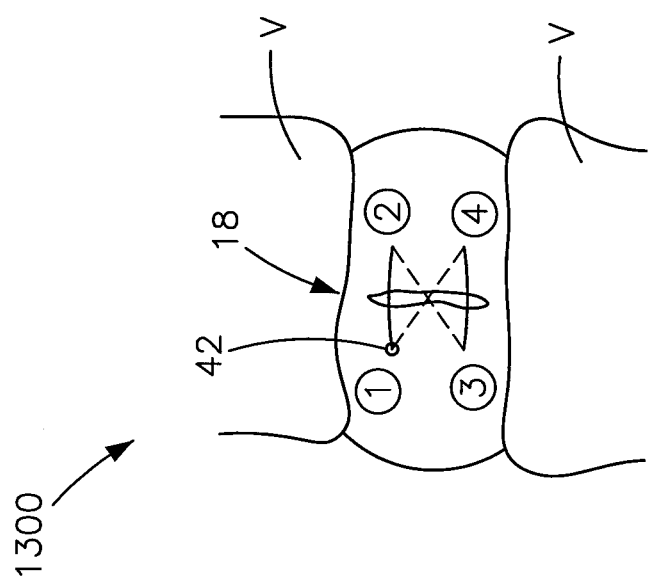
FIG. 16H is a front elevation view of an inverted vertical mattress stitch.

In reference to FIGS. 16H and 16I, an inverse vertical mattress stitch suture passing method 1300 with an interior knot 42 is illustrated. As shown, the method 1300 is similar to the vertical mattress stitch suture passing method 1200 illustrated in FIG. 16G, with the exception that the sequence of suture passing directions is reversed (exterior-to-interior becomes interior-to-exterior) to retain the knot 42 on the interior of the annulus.

Figure 16J:
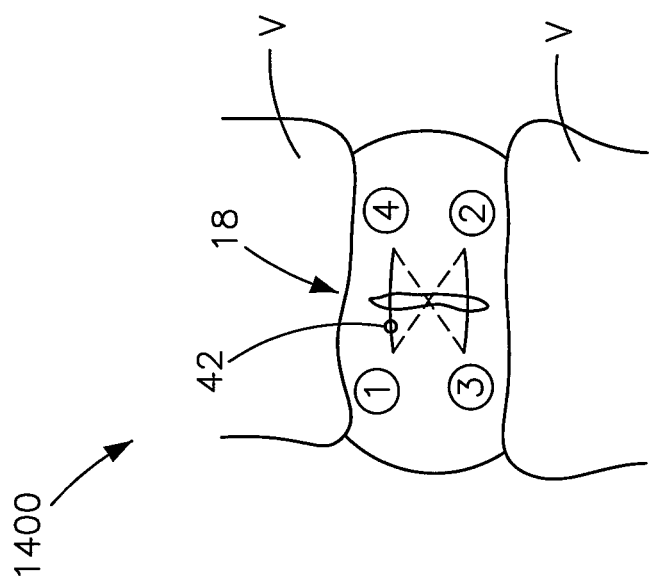
FIG. 16J is a front elevation view of a reverse vertical mattress stitch with exterior knot.

In reference to FIG. 16J, a reverse vertical mattress stitch suture passing method 1300 with exterior knot 42 is illustrated. As shown, the first free end of the suture strand is passed from the exterior to the interior of the annulus on a first side of the defect 18, then passed diagonally under the defect along the interior of the annulus to the second, opposite side of the defect 18, then retrieved from the interior to the exterior of the annulus on the second, opposite side of the defect 18, then passed horizontally over the exterior of the defect 18 back to the first side of the defect 18, then passed from the exterior to the interior of the annulus on the first side of the defect 18, then passed diagonally under the defect 18 along the interior of the annulus to the second, opposite side of the defect 18, then retrieved from the interior to the exterior of the annulus on the second opposite side of the defect 18, then passed through the knot 42. The knot 42 is then drawn to the defect 18 and is retained on the exterior of the defect 18. These method steps could be reversed (not shown) such that the sequence of suture passing directions is reversed (exterior-to-interior becomes interior-to-exterior) to retain the knot 42 on the interior of the annulus.

Utilization of the soft tissue defect repair systems described, when used in an annulus repair application, enable the defects 18 to be closed using full thickness stitches, such as are described above, which distribute suture tension across a broader portion of tissue 14, as compared to systems that distribute suture tension via tissue anchors. Providing a full thickness tissue closure, as opposed to a superficial closure that will be found with an anchoring system and in some instances with hand suturing, allows a greater healing potential of the tissue and provides a stronger barrier against immediate post-operative reherniation. Certain stitch configurations enabled by the use of the soft tissue defect repair systems of the present invention, such as vertical mattress stitches described in reference to FIG. 16G-16J, result in approximating the annular defect 18 along its entire depth by encircling the defect 18, as opposed to systems that create funnel-shaped approximated defects 18 that are formed by bridging the defect 18 at its outer surface, such approximated defects having inferior barrier properties and impaired healing potential.

Figure 17A:
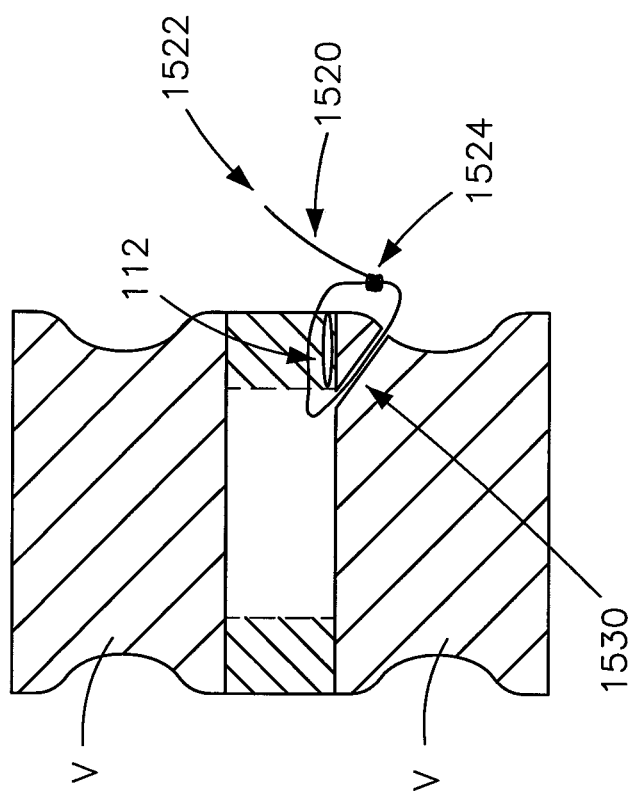
FIG. 17A is a cross-sectional view a rim tear defect inherent between the intervertebral disc and the vertebral body being approximated.

In reference to FIG. 17A, the soft tissue defect repair system 10 may be configured for repair of a soft tissue 14 defect near or adjacent to a bony element, such as an annular rim tear. FIG. 17A illustrates a pair of adjacent vertebrae V between which is disposed a disc including the soft tissue of an annulus fibrosus and the defect. The soft tissue defect repair system and method includes a trans-osseous bone tunnel 1530 that is drilled, cored, or impacted through the vertebral body V adjacent to the defect 18 to a point just interior to the annulus fibrosus, and a suture 1520 having a knot 1524 and a first free end 1522. The suture 1520, the knot 1524, and the first free end 1522 are each similar to the elements described in reference to previous embodiments.

In operation, and in continuing reference to FIG. 17A, the soft tissue defect repair system 10 may be well suited for approximating a rim tear defect 112 inherent between the intervertebral disc and the vertebral body V. To approximate the defect, one or more trans-osseous bone tunnels 1530 are formed through the vertebral body of the vertebra V adjacent the defect and into the interior of the disc space by drilling, coring, or impacting. The first free end 1522 is then passed from a first side (e.g. the exterior) to a second side (e.g. the interior) through the full thickness of the annulus on the side of the defect away from the vertebra V that is adjacent the rim tear defect. The first free end 1522 is then passed from the second side to the first side through the trans-osseous tunnel 1530. This step can be repeated if a plurality of trans-osseous tunnels 1530 is utilized in the case of a large defect. Alternately, the first free end 1522 may first be passed from a first side (e.g. the exterior) to a second side (e.g. the interior) through the trans-osseous tunnel 1530 and then from the interior to the exterior through the full thickness of the annulus tissue. The tissue is then approximated to the vertebra V adjacent the defect using any of the methods described above. These steps could be reversed such that the sequence of suture passing directions is reversed (exterior-to-interior becomes interior-to-exterior) to place the knot on the interior of the defect.

Figure 17D:
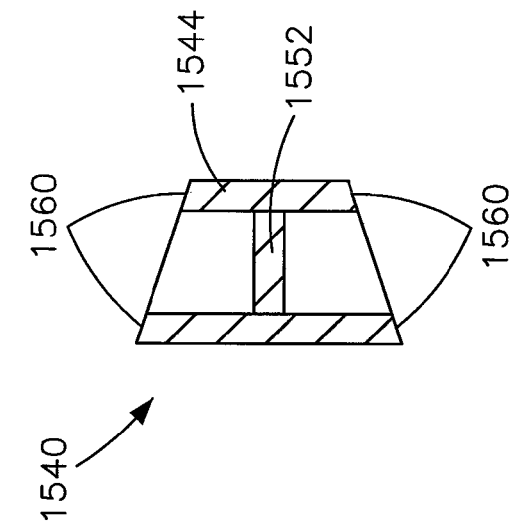
FIG. 17D is a cross-sectional view of the cannulated element of FIG. 17B having angled ends.
Figure 17B:
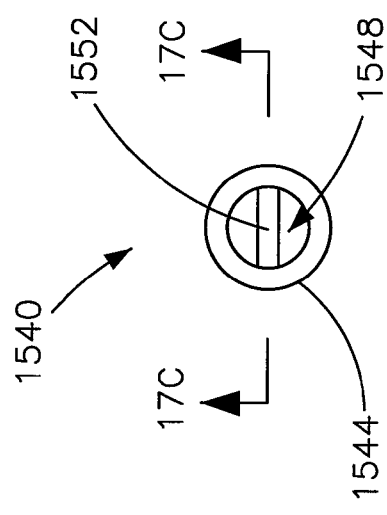
FIG. 17B is a top view of a cannulated element to be used while approximating the defect shown in FIG. 17A.
Figure 17C:
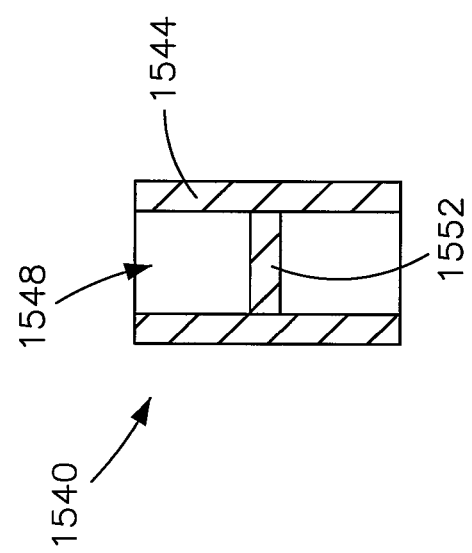
FIG. 17C is a cross-sectional view of the cannulated element shown in FIG. 17B through the line 17C-17C.
Figure 18B:
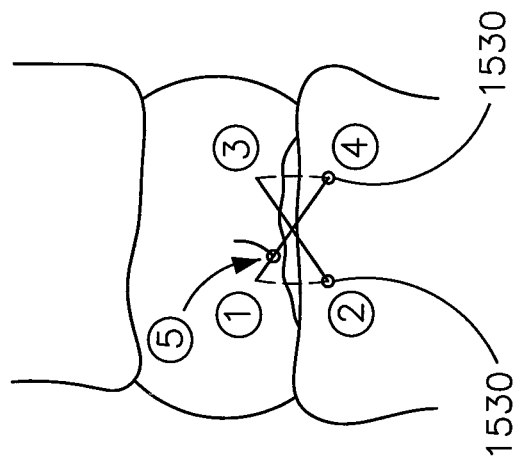
FIG. 18B is a front elevation view of a vertical mattress stitching method using the soft tissue defect repair system of FIGS. 17A-17D.
Figure 18A:
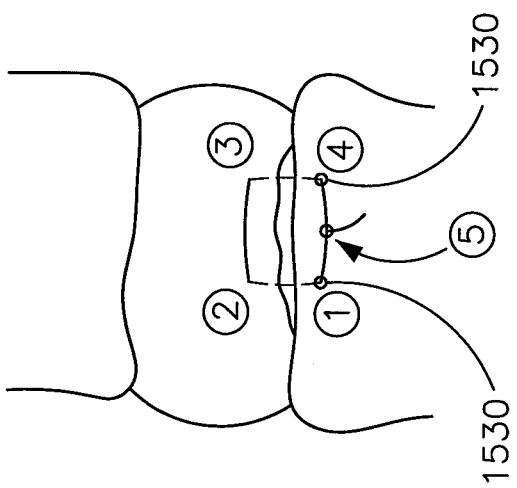
FIG. 18A is a front elevation view of a box mattress stitching method using the soft tissue defect repair system of FIGS. 17A-17D.

A threaded or press-fit cannulated element 1540 or suture anchor, as shown in FIGS. 17B and 17C, may be inserted into the trans-osseous bone tunnel 1530 prior to the suture threading step to shield the vertebra V and support loads transmitted through the suture. The cannulated element 1540 is preferably configured to span the entire length of the trans-osseous bone tunnel 1530 and achieve bi-cortical purchase. Such a cannulated element 1540 may include a cylindrical body 1544 having a bore 1548 extending therethrough, and may have an internal rod 1552 crossing the diameter of the body 1544 of the cannulated element 1540 to accommodate different numbers of sutures passed through the cannulated element 1540. As shown in FIG. 17D, such a cannulated element 1540 may further include angled ends 1560 to accommodate different approach angles. Such a cannulated element 1540 may further include an exterior threading or utilize an interference fit, such as by assuming the form of a press-fit cannulated bone dowel, to optimally secure itself within the trans-osseous bone tunnel 1530. The cannulated element 1540 may be made of allograft bone. Two front views employing mattress stitches and two trans-osseous bone tunnels 1530 are illustrated in FIGS. 18A and 18B.

Figure 19B:
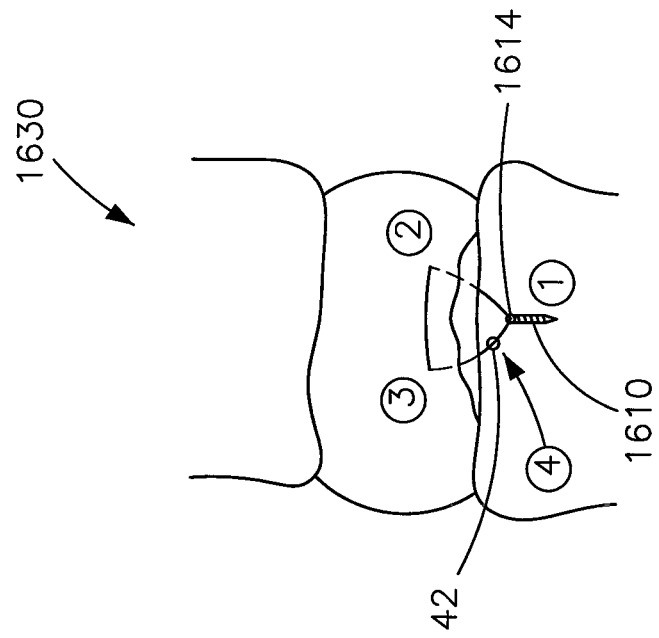
FIG. 19B is a front elevation view of the soft defect repair system of FIG. 19A with the knot being retained on the interior of the soft tissue defect.
Figure 19A:
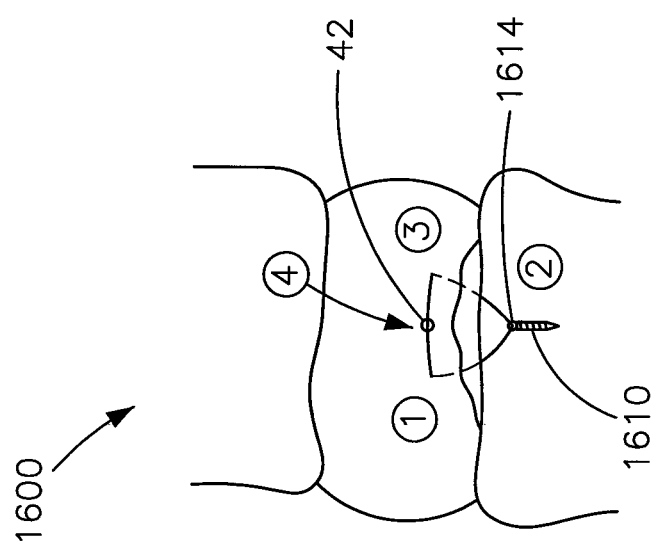
FIG. 19A is a front elevation view of another embodiment of a soft tissue defect repair system using bone anchors, in accordance with the present invention.

In another embodiment, the soft tissue defect repair system 10 may include bone anchors or suture anchors to anchor the suture to bone as shown in the rim tear methods of FIGS. 19A and 19B. As shown, a threaded or press-fit suture anchor 1610 that incorporates a suture eyelet 1614 or internal rod (such as rod 1552 in FIGS. 17A-D) can be utilized to anchor the threadable knot construct to the vertebral body adjacent the defect 18. As shown, the knot 42 may either be retained on the exterior of the approximated defect as shown for method 1600 of FIG. 19A, or interior of the approximated defect 18 as shown for method 1630 of FIG. 19B.

Figure 20A:
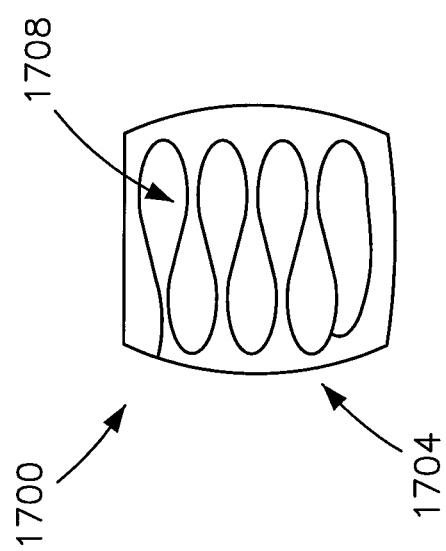
FIG. 20A is front elevational view of an embodiment of a suture plug.
Figure 20C:
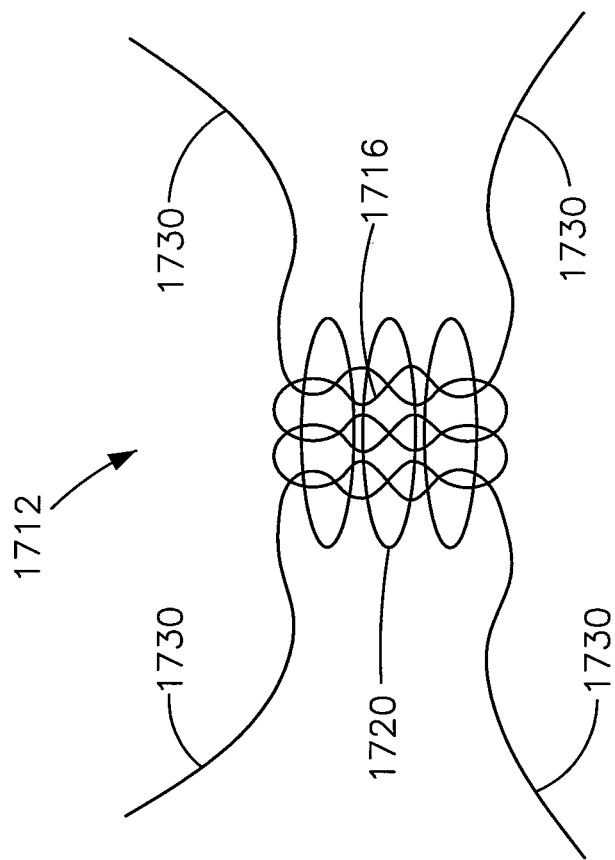
FIG. 20C is a front elevational view of the suture plug shown in FIG. 20B in a compressed state.
Figure 20B:
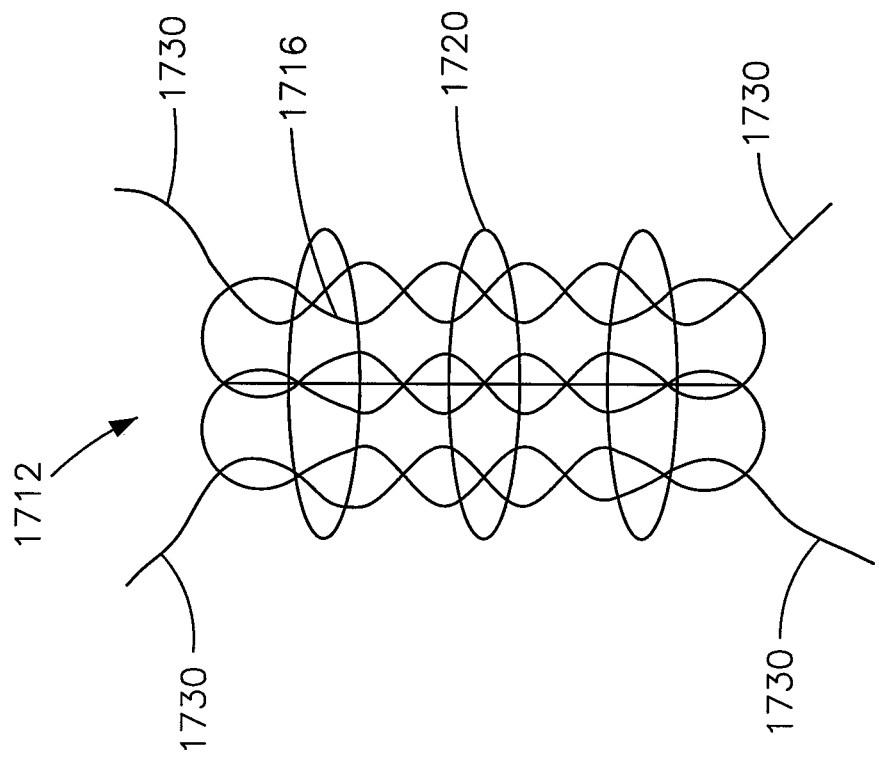
FIG. 20B is a front elevational view of another embodiment of a suture plug.

In another embodiment and in reference to FIGS. 20A-20F, the soft tissue defect repair system 10 may include a plug-type element to fill the defect 18, such as with cases in which the defect 18 is too large to approximate using sutures alone. The plug may be formed of a compliant resorbable or non-resorbable material, such as collagen, cellulose, hydrogels, polyurethanes, polyesters, etc., that acts as a scaffold to facilitate healing of the defect 18. As shown in FIG. 20A, one embodiment of a plug 1700 may include an outer woven bag 1704 filled with free strands of suture or layers of suture 1708. In another embodiment, and in reference to FIGS. 20B and 20C a plug 1712 may include strands of suture 1716 encircled by a suture loop construct 1720 to allow the tissue 14 to be cinched around the plug 1712, thereby providing a mechanical barrier. The plug 1712 can be attached to the suture loop 1720 directly or using additional elements, such as bridging sutures. The plug 1712 can be formed from suture material that is woven or braided into a structured barrier and may be layered as many times as necessary to create the desired plug height or thickness. As shown in FIGS. 20B and 20C plug 1712 may include a number of strands, such as four strands 1730 of suture extending outward. When the strands 1730 are pulled or tension is applied, the plug 1712 will compress as shown in FIG. 20C.

The plugs, including plugs 1700 and 1712, can be formed from a biocompatible material and include adhesive properties to bind the plug to the surrounding walls of the annular defect. In such an embodiment, the surface of the plug material can include inherent adhesive properties or can be induced to adhere to the surrounding tissue via the addition of an activating agent, such as UV light, aldehyde coupling agents, epoxy chemical cross-linking agents, etc. The surfaces of such plugs can further be configured to be selectively adhesive on certain surfaces and non-adhesive on other surfaces, such as those nearest to the neural structures.

Figure 20D:
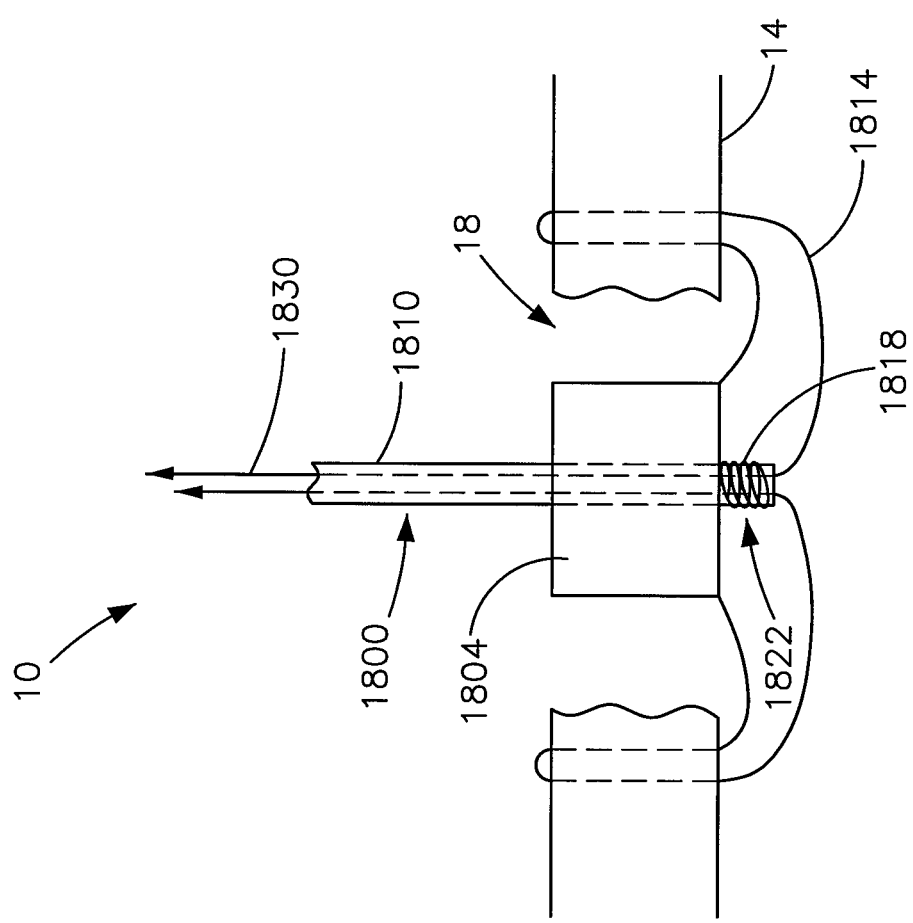
FIG. 20D is a front elevational view of another embodiment of a soft tissue defect repair system configured to place a suture plug.

As shown in FIG. 20D, soft tissue repair system 10 may include a suture finishing device 1800. As shown, the suture finishing device 1800 may include a plug 1804 (it should be understood that plug 1804 may be any type of plug including plugs 1700 and 1712 described above) positioned on a cannulated rod 1810 proximate to the distal end of the rod 1810. Accordingly, plug 1804 has a bore that extends therethrough, and the rod 1810 extends through the bore of the plug 1804. The plug bore may be compressible, such that the bore is capable of closing when the plug is slid off of the rod 1810. As shown, the suture finishing device 1800 also includes a strand of suture 1814 having a knot 1818 that is tied about a target knot location 1822 of the rod 1810. As shown, the target knot location 1822 is disposed distally from the plug position on the rod 1810. The strand of suture 1814 also has one or more free ends 1830 that may either be attached to a needle or a shuttling element.

Figure 20E:
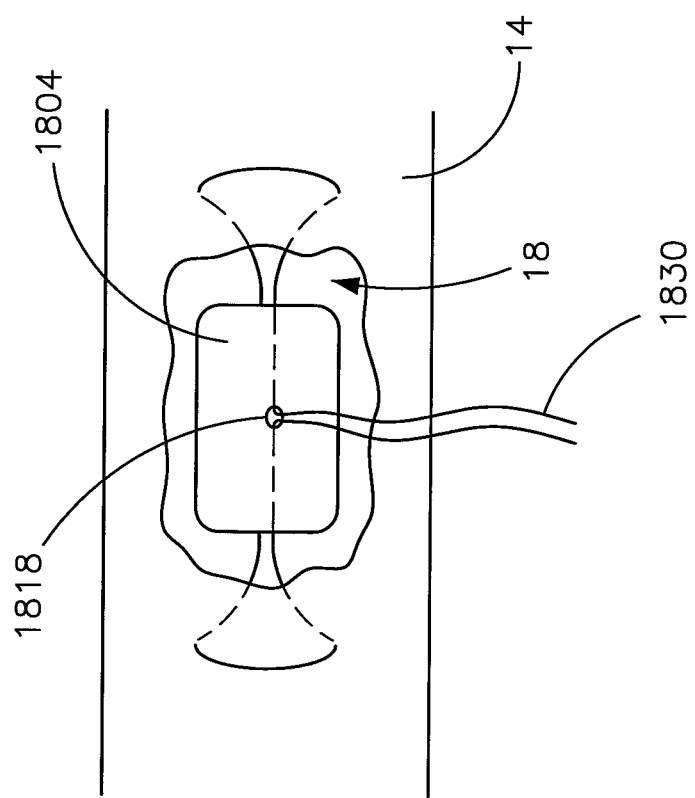
FIG. 20E is a top elevational view of the plug shown in FIG. 20D positioned in a defect after the soft tissue repair system has been removed.

In operation, the free ends 1830 of the suture strand 1814 may be passed through tissue 14 until the defect 18 is fixed. Once fixed, the needle or shuttling element may then be removed and the free ends 1830 may be pulled through a channel of the cannulated rod 1810 and out a proximal end of the rod 1810, as shown in FIG. 20D. Once through the rod 1810, the knot 1818 and plug 1804 may be pushed off a distal end of the rod 1810 as shown in FIG. 20E. As the defect is cinched closed, the plug 1804 and its compressible bore are compressed.

It should be understood that the plug may be used with any system including the system shown in FIG. 7. Therefore, the plug may include two bores and the two rods of the system shown in FIG. 7 may extend through respective bores of the plug.

Figure 20F:
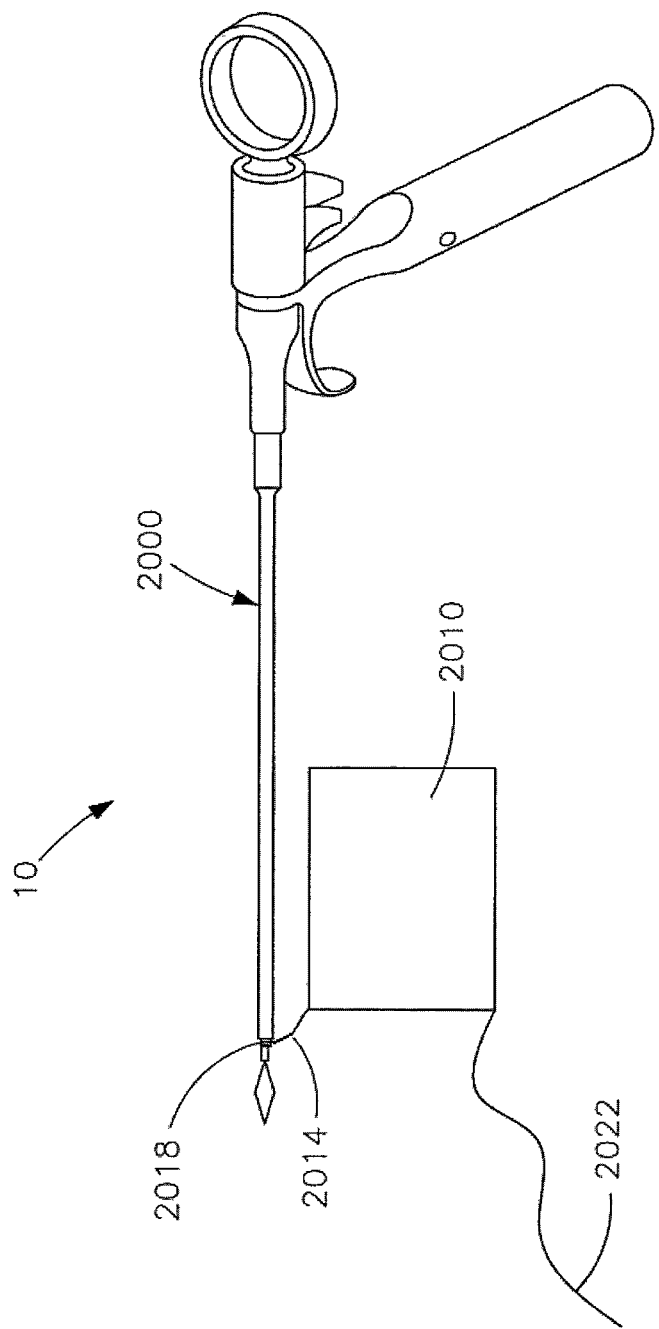
FIG. 20F is a front elevational view of another embodiment of a soft tissue defect repair system.

In another embodiment and in reference to FIG. 20F, the soft tissue repair system 10 may include suture finishing device 2000 tethered to a suture plug 2010. As shown, the soft tissue repair device 2000 also includes a strand of suture 2014 having a knot 2018 tied about a target knot location of the device 2000. The suture 2014 extends from the knot 2018 and to the suture plug 2010. The suture 2014 then extends from the plug 2010 and terminates at a first free end 2022. The first free end 2022 may be attached to a needle or to a shuttling element as described above.

Any or all of the elements previously described can be radiopaque to enable intra- and post-operative visualization via radiographic imaging. Additionally, any of the above embodiments may employ multiple threadable knot systems to repair a single defect.

Any of the soft tissue defect repair systems disclosed may be provide as a kit. For example, a system that includes a suture finishing device and a separate suture passing device may be provided as a kit, either by themselves or with strands of suture, and/or plugs.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention. Furthermore, it should be understood that any of the features of the bi-directional suture passing instruments disclosed in U.S. patent application Ser. No. 12/693,820 may be incorporated into any of the soft tissue repair systems disclosed and vice versa. For example, the engagement feature of the needle may be a wire stop that extends through a channel of the needle.

We claim:

1. A soft tissue defect repair system comprising:
    a longitudinally extending guide tube having a channel extending therethrough;
    a boom arm extending from the guide tube, the boom arm having a boom arm housing that is spaced from the guide tube, wherein a tissue-receiving gap is disposed between the boom arm housing and the guide tube;
    a needle reciprocally translatable within the channel of the guide tube between an advanced position in which a distal end of the needle extends into the boom arm housing, and a retracted position in which the distal end of the needle is retracted from the boom arm housing;
    a shuttling element configured to detachably couple to the needle, and to the boom arm housing,
    wherein an external surface of the guide tube defines a target knot location, and the shuttling element is configured to attach to a free end of a strand of suture, such that a pre-tied knot of the strand of suture is configured to be tied around the target knot location of the guide tube, such that the pre-tied knot is configured to be pushed off a distal end of the guide tube and over the free end of the suture strand so as to tighten a soft tissue defect approximated by the strand of suture.

2. The soft tissue defect repair system of claim 1, wherein the shuttling element is configured to detachably couple to a distal end of the needle.

3. The soft tissue defect repair system of claim 1, wherein the needle is configured to retract and pull the free end of the suture strand through a proximal end of the guide tube.

4. The soft tissue defect repair system of claim 1, wherein the shutting element is configured to detachably couple to an external surface of the needle.

5. The soft tissue defect repair system of claim 1, further comprising a strand of suture having a free end and a pre-tied knot, wherein the pre-tied knot is tied around the target knot location defined by the guide and the free end is attached to the shuttling element; and a plug attached to the strand of suture.

6. The soft tissue defect repair system of claim 5, wherein the plug includes strands of suture enclosed by a suture loop construct.

7. The soft tissue defect repair system of claim 5, wherein the plug comprises woven suture.

8. The soft tissue defect repair system of claim 7, wherein the woven suture is a bag.

9. The soft tissue defect repair system of claim 8, wherein the bag contains strands of suture.

10. The soft tissue defect repair system of claim 5, wherein the plug includes adhesive properties.

11. The soft tissue defect repair system of claim 5, wherein the plug is made of a biocompatible material that is configured to adhere to the surrounding tissue.

12. The soft tissue defect repair system of claim 11, wherein the material adheres to the surrounding tissue when the material is induced by an activating agent.

13. The soft tissue defect repair system of claim 5, wherein the plug is disposed around the guide tube proximate to the knot.

14. The soft tissue defect repair system of claim 1, wherein the system is configured to (i) translate the needle from its retracted position, to its advanced position, (ii) detachably couple the shuttling element to the boom arm housing, (iii) translate the needle back to its retracted position while the shuttling element is attached to the boom arm housing, (iii) translate the needle back to its advanced position, (iv) detachably couple the shuttling element back to the needle, and (v) translate the needle with the shuttling element attached thereto back to its retracted position.

15. The soft tissue defect repair system of claim 1, further comprising an adhesive applicator.

16. The soft tissue defect repair system of claim 1, further comprising a heat cutting device.

17. The soft tissue defect repair system of claim 1, wherein the knot is either a ratcheting knot, a locking knot, or a sliding knot.

18. The soft tissue defect repair system of claim 1, wherein the guide tube is a body member.

19. The soft tissue defect repair system of claim 1, wherein the tissue-receiving gap is defined by the distal end of the guide tube and the boom arm housing.

* * * * *